(12) United States Patent
Urrutia et al.

(10) Patent No.: US 11,309,084 B1
(45) Date of Patent: Apr. 19, 2022

(54) INTELLIGENT LOCATION ESTIMATION FOR ASSETS IN CLINICAL ENVIRONMENTS

(71) Applicant: Hill-Rom Services, Inc., Batesville, IN (US)

(72) Inventors: Eugene G. Urrutia, Apex, NC (US); Kenzi L. Mudge, Raleigh, NC (US); Britten J. Pipher, Fuquay-Varina, NC (US); Brandon M. Ayers, Carrboro, NC (US); Frederick Collin Davidson, Apex, NC (US); Stephen R. Embree, Chapel Hill, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 54 days.

(21) Appl. No.: 17/006,099

(22) Filed: Aug. 28, 2020

Related U.S. Application Data

(60) Provisional application No. 62/894,310, filed on Aug. 30, 2019.

(51) Int. Cl.
| | |
|---|---|
| H04W 4/029 | (2018.01) |
| G16H 40/67 | (2018.01) |
| G16H 40/20 | (2018.01) |
| H04W 4/02 | (2018.01) |
| H04W 4/021 | (2018.01) |

(52) U.S. Cl.
CPC ............ *G16H 40/67* (2018.01); *G16H 40/20* (2018.01); *H04W 4/021* (2013.01); *H04W 4/023* (2013.01); *H04W 4/027* (2013.01); *H04W 4/029* (2018.02)

(58) Field of Classification Search
None
See application file for complete search history.

(56) References Cited

U.S. PATENT DOCUMENTS

| | | | |
|---|---|---|---|
| 6,204,765 B1 * | 3/2001 | Brady | G01S 11/06 340/10.1 |
| 6,580,393 B2 | 6/2003 | Holt | |

(Continued)

OTHER PUBLICATIONS

"Asset Tracking System in Real Time," Litum, retrieved from <<https://litum.com/our-solutions/real-time-asset-tracking>> on Aug. 26, 2020, available as early as Apr. 11, 2019, 5 pages.

(Continued)

*Primary Examiner* — John F Mortell
(74) *Attorney, Agent, or Firm* — Lee & Hayes, P.C.

(57) ABSTRACT

A system can identify a first position of a tag in a clinical environment based on first times at which first receivers received a first wireless signal from the tag. The system can estimate a second position of the tag in the clinical environment based on second times at which second receivers received a second wireless signal from the tag. The system determines that a boundary is located between the first position and the second position, defines a path range around the first position of the tag based on an expected movement of the tag during a time interval between the first and second wireless signals, determines that the boundary lacks a door within the path range, adjusts the second position of the tag based on the boundary map, and transmits a message indicating that the tag is located at the adjusted position at the second time.

20 Claims, 12 Drawing Sheets

(56) References Cited

U.S. PATENT DOCUMENTS

| | | | |
|---|---|---|---|
| 7,761,347 B2* | 7/2010 | Fujisawa | G06K 7/0008 |
| | | | 705/28 |
| 7,899,006 B2 | 3/2011 | Boyd | |
| 8,031,120 B2 | 10/2011 | Smith et al. | |
| 8,830,035 B2* | 9/2014 | Lindley | G06K 7/10128 |
| | | | 340/10.34 |
| 8,838,481 B2 | 9/2014 | Moshfeghi | |
| 9,504,896 B2* | 11/2016 | Hansen | G06K 7/10475 |
| 9,513,370 B2 | 12/2016 | Cristache | |
| 9,571,143 B2 | 2/2017 | Richley | |
| 9,641,964 B2 | 5/2017 | Kulkarni et al. | |
| 9,860,688 B2 | 1/2018 | Kulkarni et al. | |
| 9,866,507 B2 | 1/2018 | Frenkel et al. | |
| 9,898,633 B2* | 2/2018 | Bottazzi | G06K 7/0008 |
| 10,423,812 B2* | 9/2019 | Enomoto | G06K 7/10316 |
| 2003/0039248 A1 | 2/2003 | Weaver | |
| 2007/0279226 A1* | 12/2007 | Whitesmith | G08B 21/023 |
| | | | 340/572.1 |
| 2008/0094228 A1 | 4/2008 | Welch et al. | |
| 2009/0015371 A1* | 1/2009 | Bocquet | G07C 9/28 |
| | | | 340/5.2 |
| 2009/0231138 A1* | 9/2009 | Lai | G06K 19/0712 |
| | | | 340/572.4 |
| 2011/0211563 A1 | 9/2011 | Herrala et al. | |
| 2013/0254304 A1 | 9/2013 | Van Nest et al. | |
| 2013/0285794 A1 | 10/2013 | Hansen | |
| 2014/0361875 A1 | 12/2014 | O'Hagan et al. | |
| 2016/0117915 A1 | 4/2016 | Llewellyn, Jr. | |

OTHER PUBLICATIONS

"Cisco Kinetic Edge & Fog Processing Module," Cisco, retrieved from <<https://www.cisco.com/c/dam/en/us/solutions/collateral/internet-of-things/cisco-kinetic-efm-whitepaper.pdf>>on Apr. 11, 2019, published Mar. 31, 2018, 26 pages.

Costin, A. et al., "Fusing Passive RFID and BIM for Increased Accuracy in Indoor Localization," Visualization in Engineering, 3:17, Dec. 2015, 20 pages.

D'Souza, M., et al., "Evaluation of Realtime People Tracking for Indoor Environments Using Ubiquitous Motion Sensors and Limited Wireless Network Infrastructure," Pervasive and Mobile Computing, vol. 9, Issue 4, Aug. 2013, Abstract, 2 pages.

D'Souza, M. et al., "Indoor Position Tracking Using Received Signal Strength-based Fingerprint Context Aware Partitioning," IET Radar, Sonar and Navigation, vol. 10, Issue 8, Oct. 2016, 18 pages.

"Function Description—Location in Ascom VoWiFi System," TD92607GB, retrieved from <<http://www.ascomwireless.com/pdf/guide/vowifi/location_vowifi_fd_92607gb.pdf>> on Apr. 15, 2019, published Dec. 13, 2010, 11 pages.

Kwan, Dennis, "Bluetooth Mesh Profile Applied to RTLS," Bluetooth Blog, retrieved from <<https://blog.bluetooth.com/bluetooth-mesh-profile-applied-to-rtls>> on Apr. 11, 2019, published Oct. 30, 2017, 5 pages.

Miekk-oja, V., "Static Beacons Based Indoor Positioning Method for Improving Room-level Accuracy," Aalto University School of Electrical Engineering, Apr. 28, 2015, 87 pages.

Najib, et al., "A Software Development Model for Localization Systems," retrieved from <<https://www.researchgate.net/publication/228343991_A_Software_Development_Model_for_Localization_Systems>> on Apr. 15, 2019, published May 2009, 6 pages.

"High-Precision RTLS," Redpoint Positioning, retrieved from <<https://www.redpointpositioning.com/wp-content/uploads/2015/06/RedpointSolutionsBrochure.pdf>> on Apr. 11, 2019, published Jun. 27, 2015, 4 pages.

Schmitt, S., et al., "The Effects of Human Body Shadowing in RF-based Indoor Localization," 2014 International Conference on Indoor Positioning and Indoor Navigation, Oct. 2014, 8 pages.

Trogh J., et al., "Enhanced Indoor Location Tracking Through Body Shadowing Compensation," Department of Information Technology, iMinds—Ghent University, Dec. 2015, 9 pages.

* cited by examiner

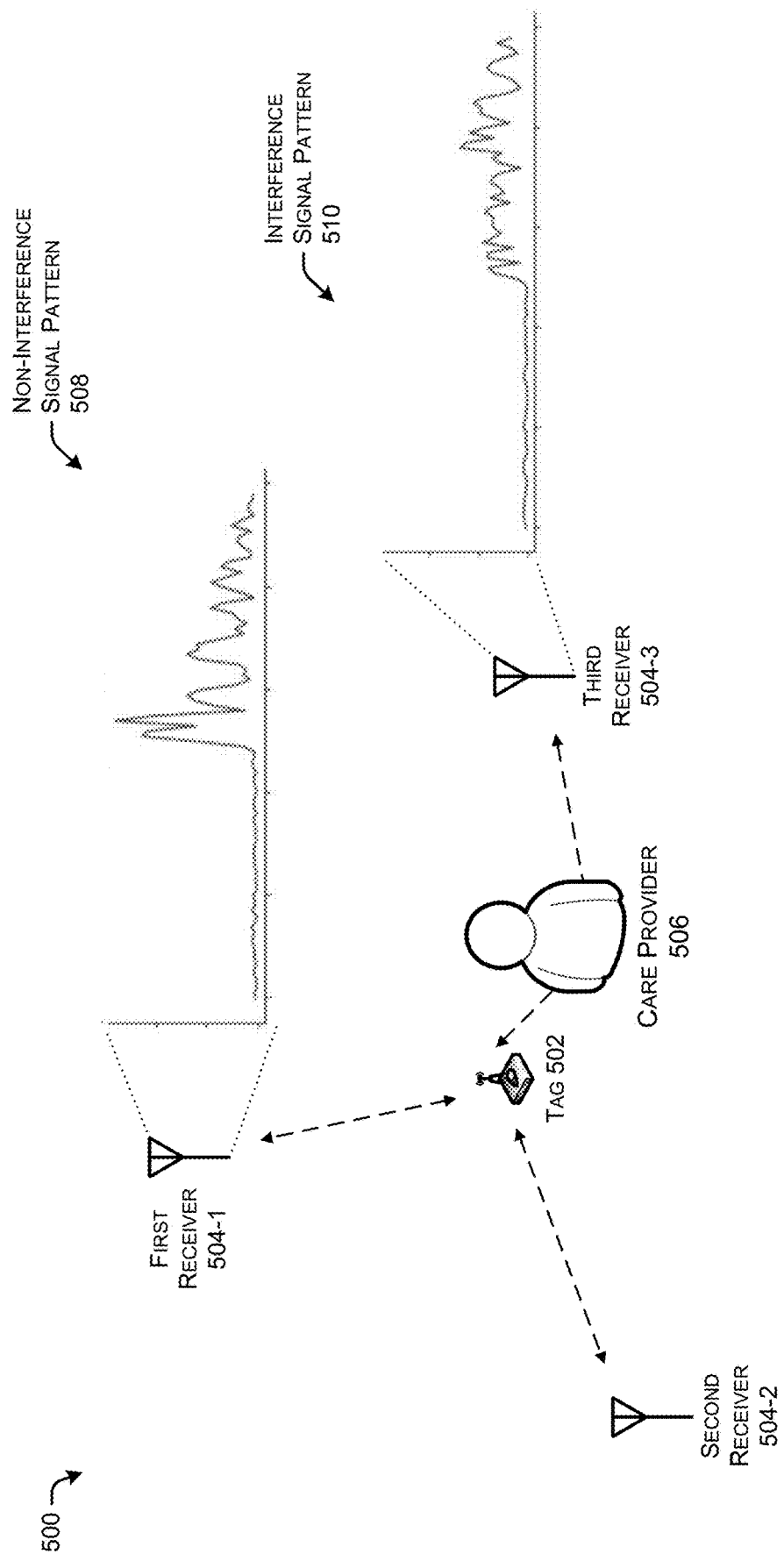

INTELLIGENT LOCATION ESTIMATION FOR ASSETS IN CLINICAL ENVIRONMENTS

CROSS-REFERENCE TO RELATED APPLICATIONS

This application claims the benefit of U.S. Provisional Application No. 62/894,310, filed on Aug. 30, 2019, which is incorporated by reference herein in its entirety.

TECHNICAL FIELD

This application relates generally to a Real Time Locating System (RTLS) configured to track the locations of assets in a clinical environment by using barrier maps to improve the accuracy of tracking and/or correcting for the influence of users on wireless signals transmitted between tags and receivers.

BACKGROUND

Hospitals, and other types of healthcare environments, track a variety of different assets, and determining/monitoring the locations of such assets can be important when administering care to patients. For instance, the positions of medical devices, hospital beds, and other clinically-relevant objects may be relevant to providing and maintaining a high level of care in these environments. In various examples, the positions of patients may be significant for managing their care. In various cases, the positions of care providers (e.g., nurses, physicians, and the like) may also be important for efficiently delivering care in the clinical environment. Tracking the positions of these and other clinically-relevant assets in real time can enable centralized systems (e.g., nurse call systems) within the clinical environment to efficiently deploy resources to care for the patients in the clinical environment.

A Real-Time Location System (RTLS) can be used to track the locations of objects and people in various settings. In the RTLS, a tag may emit a wireless signal that can be received by multiple receivers. Based on the times-of-flights (or angles-of-arrival) of the wireless signal being received by the multiple receivers, and the positions of the receivers, a tag's location can be derived within an environment.

However, broad adoption of RTLS in healthcare settings to track objects, patients, and care providers is not without challenges. There is a need for more accurate RTLS technologies adapted for various healthcare environments. In addition, due to significant variances between various healthcare environments, there is a need for a flexible RTLS platform that can be adapted for various clinical settings.

SUMMARY

Various implementations of the present disclosure relate to a location system with improved location-tracking capabilities. The system may be an RTLS. Some example implementations disclosed herein can be adapted for a healthcare environment and can be used to track the locations of assets in the environment. For instance, a system can accurately track objects (e.g., medical devices), patients, and care providers within a clinical environment.

In some instances, a location system can utilize contextual information about the physical layout of an environment to enhance its accuracy. The RTLS system may use a "boundary" (or "wall") map of the environment to determine whether measurements of a tag appear suspiciously inaccurate. For instance, if a tag appears to pass through a wall without a doorway or other threshold nearby, the RTLS system may presume that the estimated location of the tag is inaccurate and may take actions to correct the estimated location of the tag. In some cases, the RTLS system may correct the estimated location of the tag based on the boundary map. For instance, the system may adjust the estimated location of the tag to be on the same side of the wall as its last known location.

In some implementations, a location system tracking a tag worn by, carried by, or otherwise attached to a person can correct for the influence of the person on the propagation of a signal emitted by the tag. In various cases, the signal may be attenuated, slowed down, and/or refracted as it encounters the person's body. The system may identify whether the person is located between a particular receiver and the tag as the tag is transmitting the wireless signal to the receiver. The system may estimate the influence of the person's body on how the wireless signal is received by the receiver. When the measurements (e.g., the time at which it receives) the wireless signal, the system may automatically adjust those measurements based on the influence of the person's body.

Various implementations disclosed herein provide technical improvements to the fields of RTLS-based tracking. In particular, various implementations can be used to more accurately track assets in a clinical environment, such as a hospital.

DESCRIPTION OF THE FIGURES

The following figures, which form a part of this disclosure, are illustrative of described technology and are not meant to limit the scope of the claims in any manner.

FIG. 5 illustrates an example location system environment for correcting the estimated position of a tag based on the position of a person associated with the tag.

DETAILED DESCRIPTION

Figure 1:
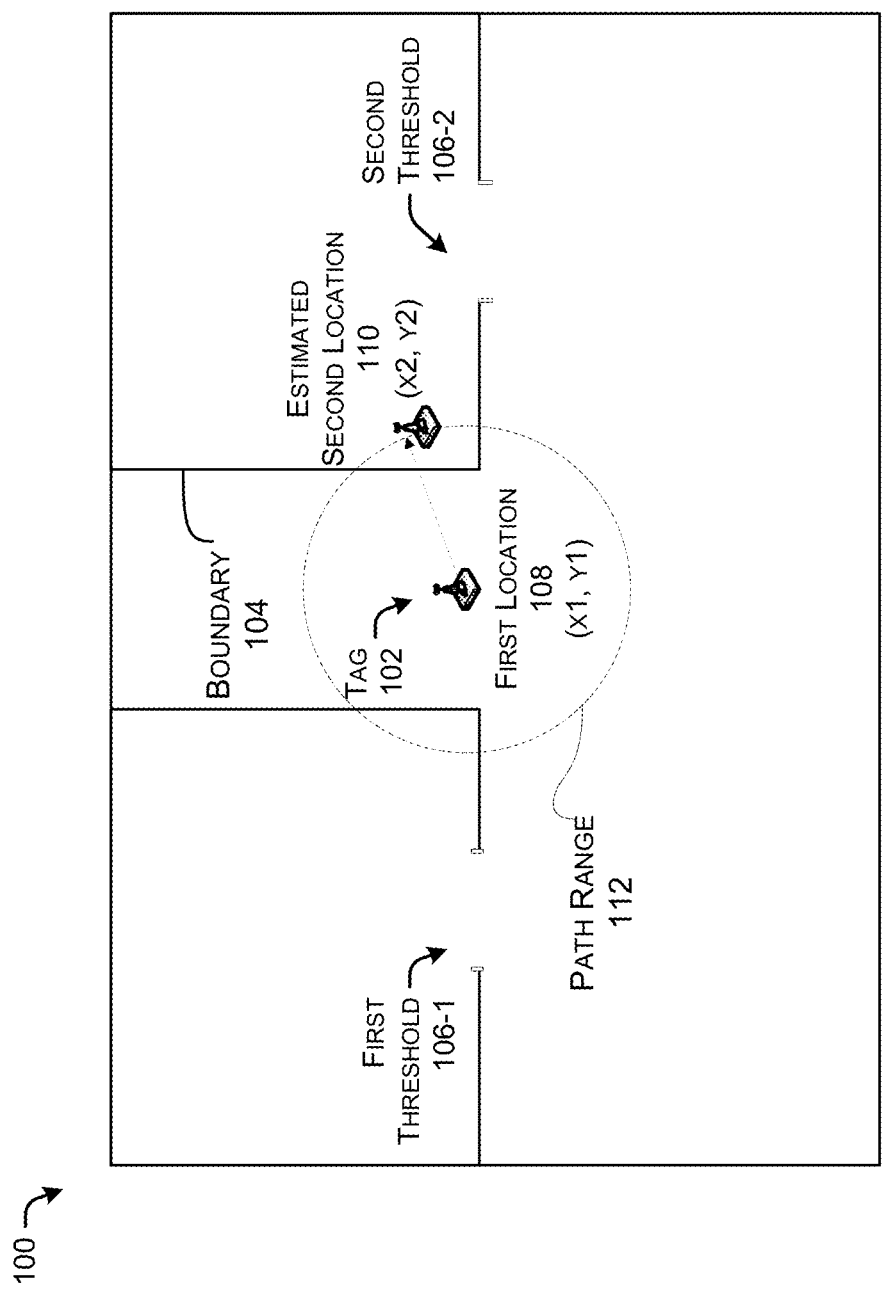
FIG. 1 illustrates an example clinical environment for tracking the location of an asset.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

FIG. 1 illustrates an example clinical environment 100 for tracking the location of an asset in a clinical environment. The asset may be associated with a tag 102. As used herein, the term "tag" can refer to a physical device capable of storing information, transmitting information to a remote device, and/or receiving information from a remote device. A tag may be attached to a physical object (e.g., a medical device, a hospital bed, or the like). In various implementations, a tag can be passive, such that it collects energy from outside sources (e.g., radio waves) to power storage, data transmission, processing, or the like. In some implementations, a tag can be active, such that it may include a power source that can be used to power storage, data transmission, processing, or the like. Some examples of tags include Radio-Frequency Identification (RFID) tags, which can use electromagnetic signals to communicate with external devices. However, some tags can use non-radio-frequency electromagnetic signals, acoustic signals, or the like to communicate with external devices.

In some cases in which the asset is an object (e.g., a medical device, a hospital bed, or the like), the tag 102 may be attached to the object. In some instances in which the asset is a person (e.g., a patient, care provider, or the like), the tag 102 may be worn by the person. In some instances, the tag may be worn on a lanyard or necklace around the person's neck. In some examples, the tag may be integrated into a wristband that is worn by the person. In some instances, the tag may be integrated into clothes worn by the person.

According to some example implementations, the clinical environment 100 may be a floor of a building. In some cases, the clinical environment 100 may have at least one boundary 104, which may be a wall or the like. Further, the boundary 104 may be a fence, a window, or some other solid boundary that solid objects cannot easily pass through. Although FIG. 1 illustrates a single, continuous boundary 104, various implementations can include multiple boundaries. In addition, throughout the clinical environment 100, the boundary 104 may be interrupted by thresholds, such as a first threshold 106-1 and second threshold 106-2. As used herein, the term "threshold" may refer to a door, a gate, an opening, a window, or any other break in the boundary 104 that can be traversed by solid objects.

In various implementations, the boundary 104 and the thresholds 106-1 and 106-2 can be identified using a boundary map. The boundary map may represent the locations of various boundaries and thresholds within the environment 100. In some cases in which the environment 100 is represented in two dimensions, the boundary map can represent the locations of the boundary 104 and the thresholds 106-1 and 106-2 within an x-y coordinate system. A location system, such an RTLS, can utilize the boundary map to accurately predict the location of the tag 102 and the asset. Various examples of a location system are described below with reference to FIGS. 7 to 11. In some implementations, the location system can include a system or a device that includes at least one processor executing various instructions stored in memory. Accordingly, actions performed by the location system can be performed by the processor(s) in the location system.

In various implementations, the tag 102 may be identified at a first location 108 within the environment 100 by the location system. The first location 108 may be represented in the x-y coordinate system by the coordinates $(x_1, y_1)$. In addition, the tag 102 may be estimated to be at a second location 110 within the environment 100 by the location system. The second location may be represented in the x-y coordinate system by the coordinates $(x_2, y_2)$. The location system may determine first location 108 by a first wireless signal transmitted by the tag 102 and determine the estimated second location 110 based on a second wireless signal transmitted by the tag 102. The first wireless signal may be generated and/or sent before the second wireless signal. In some cases, the first and second wireless signals are consecutive signals transmitted by the tag 102. Accordingly, the estimated second location 110 may be estimated to be a subsequent position of the tag 102 after the tag 102 is located at the first location 108.

In example implementations, the system may identify and/or estimate the locations of the tag 102 by performing trilateration, multilateration, triangulation, or the like. For example, the location system can determine time lags of the wireless signals transmitted between the tag 102 and various receivers associated with the location systems based on the transmission times and the reception times (or based on a one-way transmission time derived from a Round Trip Time (RTT)), and can determine the distances between the tag 102 and the receivers by multiplying the time lags by the velocity of the wireless signals. In some cases, the locations of the tag 102 can be derived based on discrepancies between reception times of the same wireless signal by different receivers in the environment 100. Some example instances are described in more detail below with reference to FIG. 7.

Using the boundary map, the location system may identify that the boundary 104 is located between the first location 108 and the estimated second location 110. For instance, the RTLS may determine that a line segment defined between the first location 108 and the estimated second location 110 intersects the boundary 104 by comparing the line to the boundary map. Because the tag 102 cannot cross the boundary 104 without a break (e.g., a threshold) within the boundary 104, the location system may perform additional actions to confirm whether the estimated second location 110 is accurate.

The location system may confirm whether the tag 102 may have traversed a threshold (e.g., the first threshold 106-1 or the second threshold 106-2) in the boundary 104 in order to cross the boundary 103 and arrive at the estimated second location 110. In some implementations, the location system may determine an expected range of movement of the tag 102 in a time interval between the first wireless signal and the second wireless signal. For instance, if the tag 102 is associated with a care provider, the expected range of movement of the tag 102 may be a walking speed of the care provider multiplied by the time interval. In some cases, the walking speed can be estimated based on a predetermined walking speed, such as 5 miles per hour. In various examples, the walking speed can be estimated based on previously tracked movements of the care provider. For instance, if the care provider has previously moved at a pace of 7 miles per hour, the walking speed may be 7 miles per hour. In some instances, the walking speed may be an average speed of the care provider, a maximum speed of the care provider, or a combination thereof.

The location system may also estimate an expected range of error associated with its own capabilities of estimating the location of the tag 102. For instance, the expected range of error can be determined based on historical trends, the density of receivers picking up the first and second signals within the environment 100, a sensitivity of the receivers picking up the first and second signals, or the like. According to some examples, the expected range of error is calculated by preliminarily testing the location system's accuracy. For instance, the tag 102 may be placed in a known location, the location system may estimate the position of the tag 102 to generate an estimated location, and the known location and the estimated location can be compared. In some cases, the expected range of error can be added to the expected range of movement of the tag 102. Based on the expected range of movement of the tag 102, the location system may determine a path range 112 representing an expected range of paths that the tag 102 could move in the time interval between transmitting the first signal and the second signal. The path range 112 may be represented by a circle, an ellipse, a square, and/or any other shape that is centered at the first location 108. In some cases, a radius of the path range 112 can be the sum of the expected range of movement and the expected range of error of the location system.

In various implementations, the location system may determine whether a threshold in the boundary 104 exists at least partly within the path range 112. If a threshold, such as the first threshold 106-1 or the second threshold 106-2, is located at least partly within the path range 112, then the RTLS may determine that there is a possible path by which the tag 102 traversed the boundary 104. Such a path may extend, for example, from a previous location of the tag 102 to an additional location of the tag 102 (e.g., to the estimated second location 110), and such a path may pass through the threshold disposed at least partly within the path range 112. When a threshold is determined to be within the path range 112, the location system may confirm that the second location 110 is accurate and report the estimated second location 110 as the location of the tag 102.

However, as shown in FIG. 1, the boundary 104 may lack a threshold within the path range 112. That is, the second threshold 106-2 in the boundary 104 is not even partly located within the path range 112. When the location system determines that the boundary 104 lacks a threshold within the path range 112, the location system may identify that the estimated second location 110 is inaccurate. The location system may correct the estimated second location 110.

Figure 2:
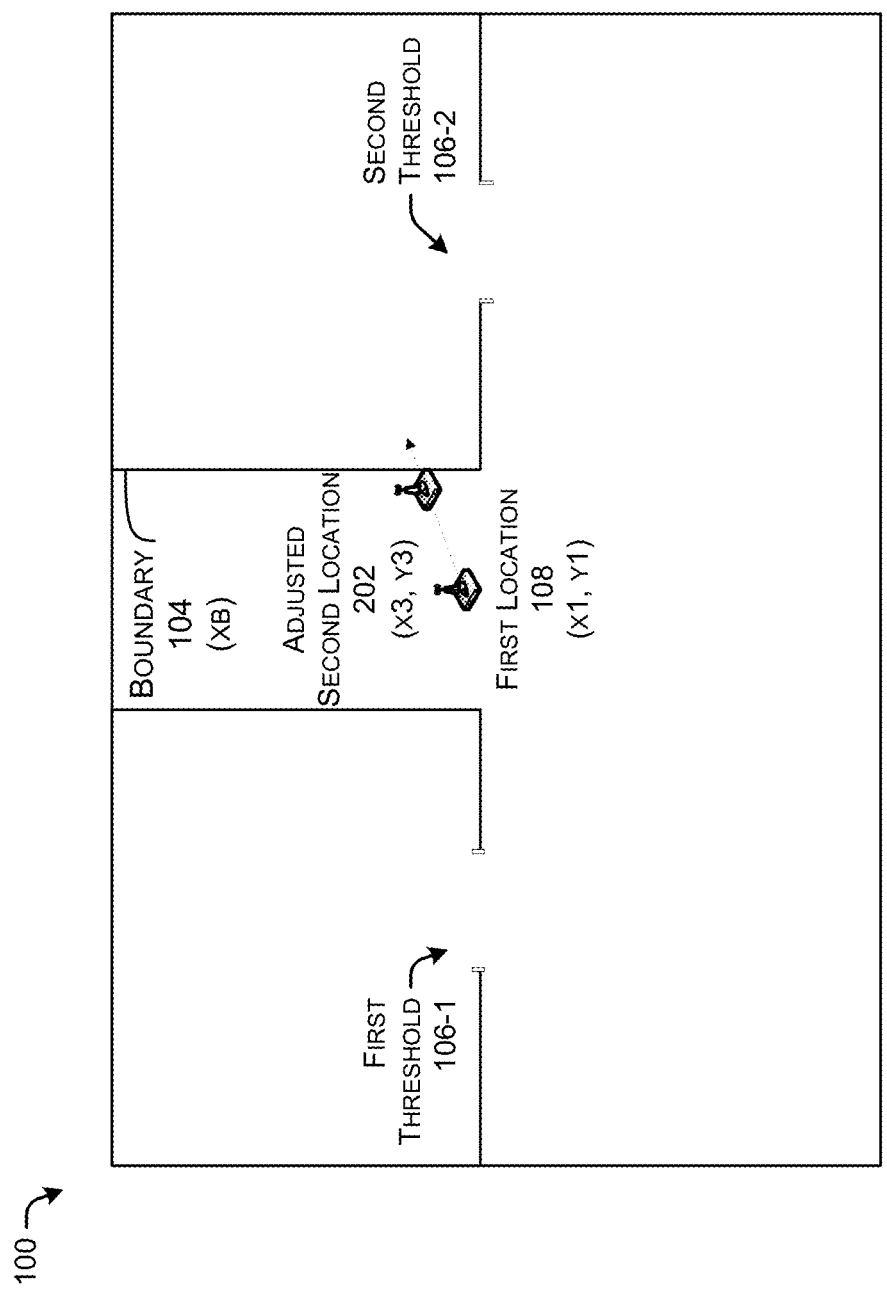
FIG. 2 illustrates an example environment indicating how a subsequent location can be corrected according to various implementations of the present disclosure.

FIG. 2 illustrates an example environment 200 indicating how the second location 110 can be corrected according to various implementations of the present disclosure. In various implementations, upon identifying that the boundary 104 lacks a threshold within the path range 112, the location may identify an adjusted second location 202 of the tag 102 based on the boundary map. The adjusted second location 202 may also be referred to as a "corrected second location 202." The adjusted second location 202 may be on the same side of the boundary 104 as the first location 108. That is, the boundary 104 may not be disposed between the first location 108 and the adjusted second location 202. The adjusted second location 202 may be represented in the x-y coordinate system by the coordinates $(x_3, y_3)$.

In various implementations, the adjusted second location 202 may lie on the line segment defined between the first location 108 and the estimated second location 110. In some example implementations, the line segment may be defined by the following Formula 1:

$$y_n = \left(\frac{y_2 - y_1}{x_2 - x_1}\right) x_n + \left(\frac{x_1 y_2 - x_2 y_1}{x_2 - x_1}\right) \quad \text{Formula 1}$$

wherein $(x_n, y_n)$ represents any point on the line segment. Accordingly, the corrected location may be one example of $(x_n, y_n)$ coordinates.

In some examples, the location system may determine the adjusted second location 202 by decreasing the distance between the first location 108 and the estimated second location 110 by consecutive percentages until the first location and the adjusted second location 202 are located on the same side of the boundary 104. For instance, the location system may decrease the distance by a percentage (e.g., 5%, 10%, or the like) and check whether the percentage adjustment would place the adjusted second location 202 on the same side of the boundary 104 as the first location 108. If the percentage adjustment is sufficient, the location system may confirm the adjusted second location 202. If the percentage adjustment is insufficient, the location system may perform an additional adjustment on the adjusted second location 202 (e.g., a decrease in the distance by another 5%, 10%, or the like).

In various implementations, the location system may use the coordinates of the boundary 104 provided in the boundary map to automatically generate the adjusted second location 202. The location system may identify that the boundary 104 is represented by a series of x-y coordinates, or by an equation within the x-y coordinate system. For instance, the boundary 104 depicted in FIG. 1 may be defined according to a dataset of x-y coordinates. The coordinates of the first location 108 $(x_1, y_1)$ may be compared to the dataset of the boundary 104, to determine whether $x_1$ is less than, equal to, or greater than the x coordinates of the dataset representing the boundary 104 and whether $y_1$ is less than, equal to, or greater than the y coordinates of the dataset representing the boundary 104. In the implementation depicted in FIG. 2, the $x_1$ value of the first location 108 may be less than the x coordinates of the dataset. Accordingly, the location system may identify that the $x_3$ value of the adjusted second location 202 should also be less than the x coordinates of the boundary 104.

In some cases, the location system may input the dataset representing the boundary 104 into Formula 1, in order to find the point of intersection between the line segment and the boundary 104. In some cases, the location system may define the adjusted second location 202 to be at the point of intersection, or slightly (e.g., half the thickness of the boundary, such as 4 inches or the like) toward the first location 108 from the boundary 104. In some cases, the boundary map defines both surfaces of the boundary 104. Accordingly, the adjusted second location 202 may be defined according to the inner surface of the boundary 104 facing the first location 108.

In an example, because boundary 104 is defined vertically in the x-y coordinate system, the boundary map may indicate that an inner surface of the boundary 104 is represented by $x_b = a$, wherein $d < y_b < e$, and a, d, and e are each constants. The location system may input the value of $x_b = a$ as the $x_n$ value of Formula 1 to calculate a corresponding)), value. The coordinates $(x_3, y_3)$ can be defined such that $x_3 = x_b$ (or slightly less than $x_b$), and $y_3 =$ the corresponding $y_n$ value.

Various clinical environments, such as environment 100, have numerous boundaries (e.g., boundary 104) that make it difficult to accurately assessing the location of tags (e.g., the tag 102) based on wireless signals between the tags and the receivers. Boundaries may attenuate, reflect, and/or slow down wireless signals, thereby lowering the accuracy of the location system. According to various implementations described herein, the location system can confirm and/or correct the estimated location of the tag 102 based on a boundary map of the environment 100. The accuracy of the location system can therefore be improved.

Figure 3:
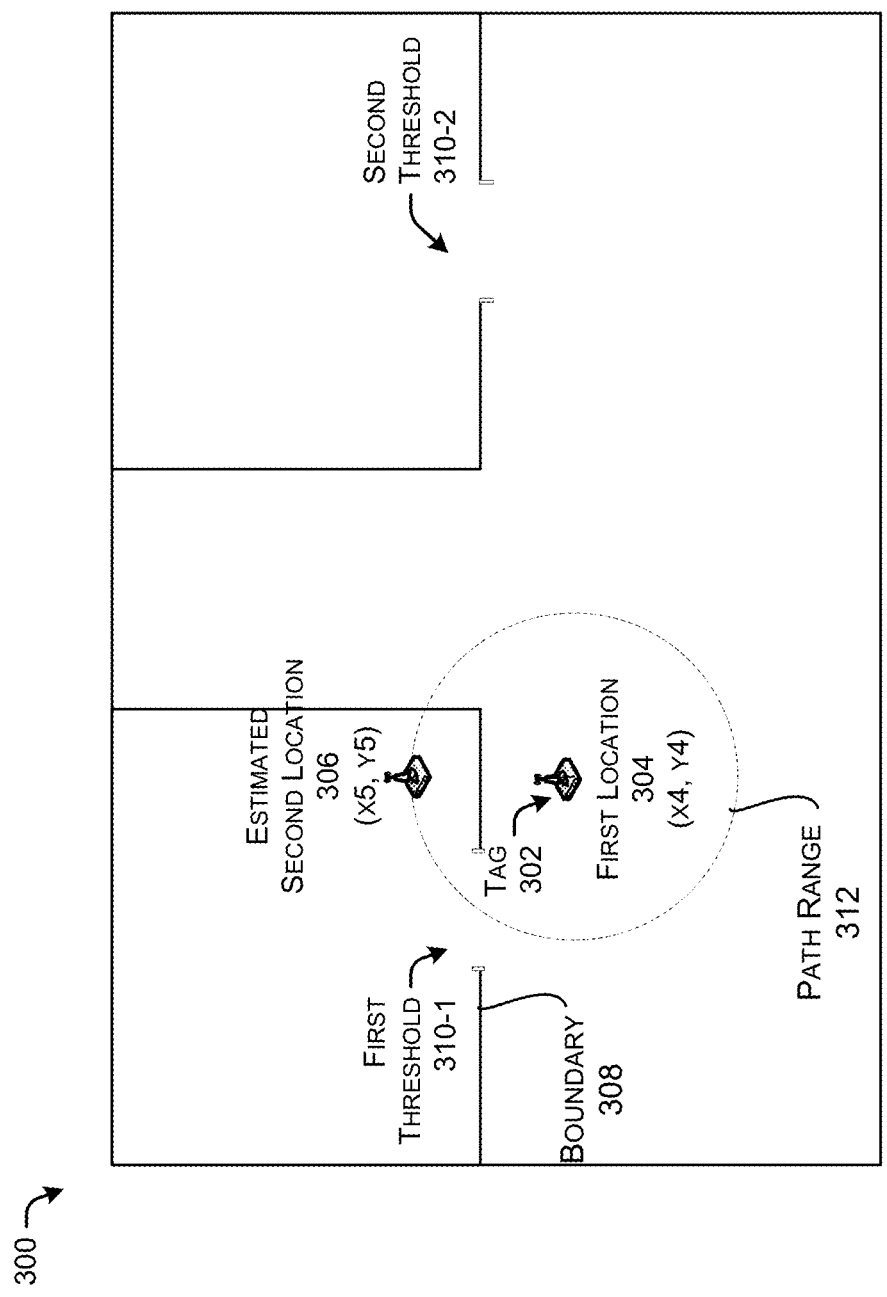
FIG. 3 illustrates an example environment in which a location system confirms a subsequent location of a tag that has moved from one side of a boundary to another.

FIG. 3 illustrates an example environment 300 in which a location system confirms a subsequent location of a tag that has moved from one side of a boundary to another. Similar to FIGS. 1 and 2, the environment 300 includes a tag 302 that is determined to move from a first location 304 (defined by the coordinates ($x_4$, $y_4$)) to an estimated second location 306 (defined by the coordinates ($x_5$, $y_5$)). The environment 300 may include a boundary 302 with various thresholds, such as a first threshold 310-1 and a second threshold 310-2. The location system may be an RTLS. In various implementations, the location system may include at least one processor that executes various instructions stored in memory. Accordingly, actions of the location system can be performed by the processor(s).

The location system may identify that the boundary 308 exists between the first location 304 and the estimated second location 306 using a boundary map of the environment 300. The location system may identify a path range 312 around the first location 304. However, unlike the implementations discussed illustrated in FIGS. 1 and 2, the location system may determine that the first threshold 310-1 is at least partially within the path range 312. The location system may make this determination using the boundary map. Upon determining that the first threshold 310-1 is in the path range 312, the location system may confirm the estimated second location 306 as the position of the tag 302.

Figure 4:
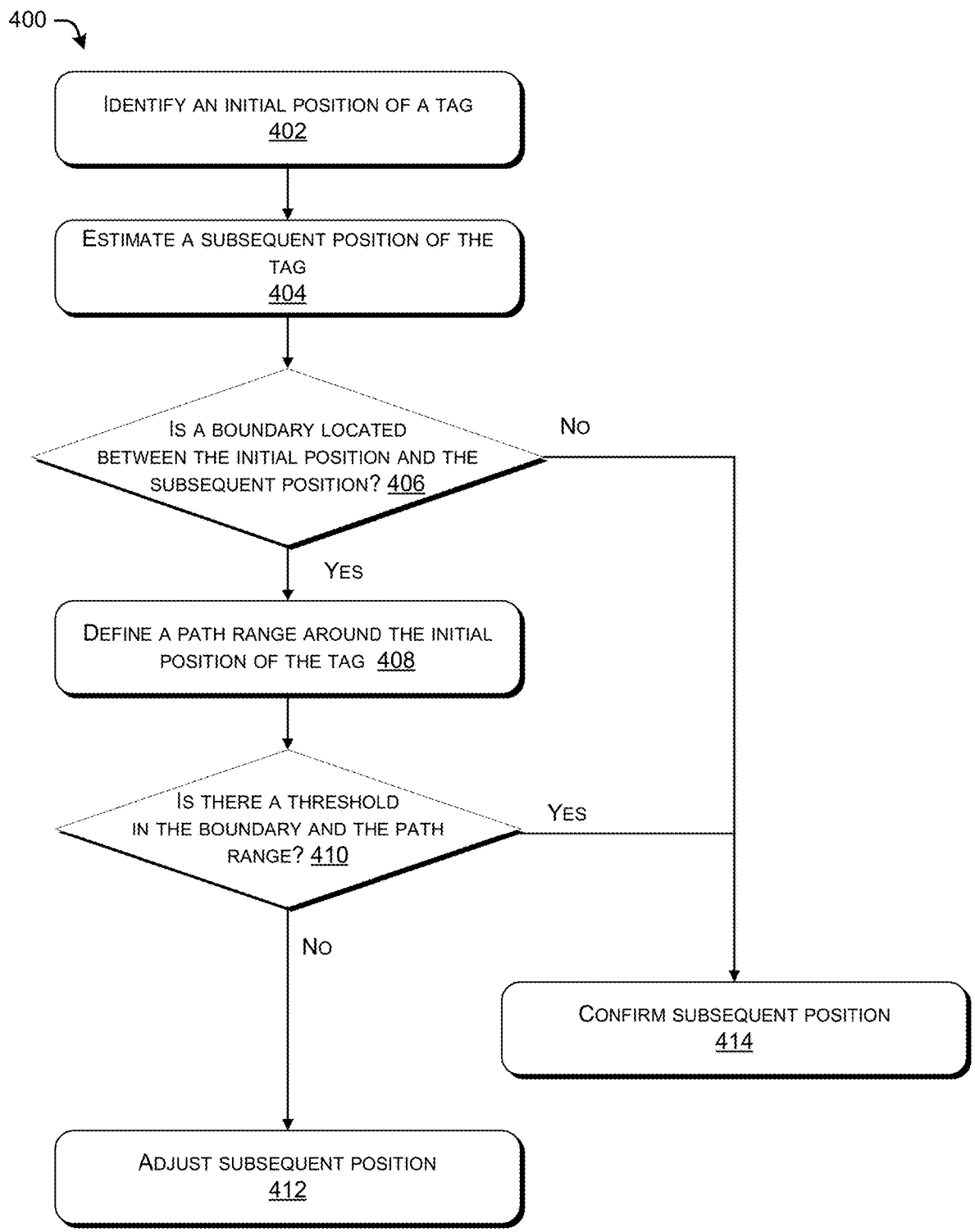
FIG. 4 illustrates an example process that can be performed by a location system.

FIG. 4 illustrates an example process 400 that can be performed by a location system. For instance, the process 400 can be performed by the location system 808 described below with reference to FIGS. 8 to 10, the location engines 1006 or 1108 described below with reference to FIGS. 10 and 11, or any other suitable RTLS.

At 402, the system may identify an initial position of the tag. The system may identify the initial position based on the transmission of a first signal from the tag to multiple receivers in an environment. Based on the times at which the receivers receive the first signal, as well as the positions of the receivers, the system may identify the initial position of the tag.

At 404, the system may estimate a subsequent position of the tag. The system may estimate the subsequent position based on the transmission of a second signal from the tag to multiple receivers in the environment. In some cases, the tag may transmit the second signal after the first signal. Based on the times at which the receivers receive the second signal, as well as the positions of the receivers, the system may estimate the subsequent position of the tag.

At 406, the system may determine whether a boundary is located between the initial position and the subsequent position. In some cases, the system can reference a boundary map associated with the environment in order to identify whether the boundary is present between the initial position and the subsequent position. For instance, the system may compare a line segment between the initial position and the estimated subsequent position to the boundary map in order to determine whether the line segment intersects a boundary in the environment.

If the system determines that the boundary is located between the initial position and the subsequent position at 406, the system may define a path range around the initial position at 408. The path range may have a radius that depends on an expected range of movement of the tag. In some cases, the expected range of movement can be based on a movement speed of a care provider associated with the tag and/or a time interval between the wireless signals used to identify the initial position and estimate the subsequent position. For instance, the radius of the path range can be equal to the sum of the expected range of movement and the expected range of error of the RTLS system. The system may define the path range to be centered around the initial position.

At 410, the system may determine whether there is a threshold in the boundary and the path range. For instance, the system may reference the boundary map in order to identify whether a threshold in the boundary is present within the path range. The system may determine that there is a threshold in the path range if a threshold in the boundary is at least partly within the path range.

If the system determines that the boundary lacks a threshold within the path range at 410, the system may adjust the subsequent position at 412. In some cases, the system may adjust the subsequent position to be at a surface of the boundary facing the initial position. In some cases, the system may adjust the subsequent position to be on the same side of the boundary as the initial position.

If, however, the system determines that a boundary is not located between the initial position and the subsequent position at 406, or the system determines that there is a threshold in the boundary within the path range at 410, the system may confirm the subsequent position at 414. In some cases, the system may transmit a message to a reporting system that indicates the subsequent position as the true position of the tag.

FIG. 5 illustrates an example location system environment 500 for correcting the estimated position of a tag 502 based on the position of a person associated with the tag 502. The location system may be an RTLS, in some cases. In various implementations, the tag 502 can transmit wireless (e.g., radio) signals to various receivers in a clinical environment. For instance, as illustrated in FIG. 5, the tag 502 transmits a wireless signal to a first receiver 504-1, a second receiver 504-2, and a third receiver 504-3 in the environment 500.

In general, a system can presume that the wireless signal is transmitted in a straight line through ambient air. However, as illustrated in FIG. 5, the tag 502 may be associated with a care provider 506 whose body is not made of air. The wireless signal may propagate through the air at a different phase velocity than through the body of the care provider 506. The air may have a different index of refraction than the body of the care provider 506, with respect to the wireless signal. Accordingly, when the wireless signal is intercepted by the body of the care provider 506, the wireless signal may be refracted. Specifically, because the care provider 506 is located between the tag 502 and the third receiver 504-3, the wireless signal may travel a greater distance and at a slower speed to get to the third receiver 504-3, than if the body of the care provider 506 was not between the tag 502 and the third receiver 504-3. That is, the time at which the third receiver 504-3 receives the wireless signal may be delayed.

When the wireless signal is refracted by the body of the care provider 506, the wireless signal may slow down and/or change direction. If the location system calculates the position of the tag 502 based on the time-of-flight of the wireless signal as it is transmitted from the tag to the receivers 504-1 to 504-3, the angle-of-incidence of the wireless signal as it is received by the receivers 504-1 to 504-3, discrepancies between times at which the wireless signal is received by the receivers 504-1 to 504-3, or the like, the location system may inaccurately estimate the location of the tag 502 without accounting for a delay associated with the refraction of the wireless signal.

In various implementations, the location system may predict an amount that the wireless signal is delayed due to the presence of the care provider 506. In some cases, the location system may associate a signal pattern of the wireless signal as it is received by one of the receivers 504-1 to 504-3 with the delay. For instance, the location system may implement a machine learning model that can identify features in the signal pattern indicating whether the wireless signal has passed through the care provider 506 during transmission. The machine learning model can be trained based on testing data including signal patterns with known physical interference levels (e.g., the interception levels of the wireless signals by care providers or other users are known).

The wireless signal, as transmitted by the tag 502, may be an Ultra-Wideband (UWB) signal. In accordance with the IEE 802.15.4 standard, an UWB signal can be transmitted as a burst of pulses positioned within the signal's period. However, the wireless signal may be received differently than it is transmitted. As illustrated in FIG. 5, the first receiver 504-1 may receive the wireless signal with a non-interference signal pattern 508. The non-interference signal pattern 508 may be represented as a digital amplitude of the received wireless signal versus an accumulator sample index. The non-interference signal pattern 508, as well as other wireless signals that are transmitted directly from the tag 502 to one of the receivers 504-1 to 504-3 without passing through the care provider 506, may have relatively tall, sharp peaks at the beginning of its duration. For instance, an arithmetic mean of the first 30% of the indices of the non-interference signal pattern 506 may be over twice the level of the arithmetic mean of the last 70% of the indices of the non-interference signal pattern 506.

In contrast, the third receiver 504-3 may receive the same wireless signal with an interference signal pattern 510. The interference signal pattern 510 may be represented as digital amplitude of the received wireless signal versus an accumulator sample index. The interference signal pattern 510 may indicate that the wireless signal has passed through the body of the care provider 506. For instance, unlike the non-interference signal pattern 508, the interference signal pattern 510 may lack the sharp peak(s) at the beginning of the of its duration. In some examples, an arithmetic mean of a first percentage (e.g., the first 30%) of the indices of the interference signal pattern 510 may be less than twice the level of the arithmetic mean of a las percentage (e.g., the last 70%) of the indices of the interference signal pattern 510. Due to the differences in the shape between the non-interference signal pattern 508 and the interference signal pattern 510, the location system (e.g., utilizing the machine learning model) may be able to identify that the care provider 506 was not present between the tag 502 and the first receiver 504-1 when the wireless signal was transmitted between the tag 502 and the first receiver 504-1 and/or that the care provider 506 was present between the tag 502 and the third receiver 504-3 when the wireless signal was transmitted between the tag 502 and the third receiver 504-3. In some cases, the location system can utilize a machine learning model to identify the presence or absence of the care provider 506 in the path of a wireless signal received by the first receiver 504-1, the second receiver 504-2, the third receiver 504-3, or any combination thereof.

In addition, the location system may predict a delay in the reception time of the wireless signal by the third receiver 504-3 due to the traversal of the care provider 506 by the wireless signal. For instance, the location system may input the shape of the wireless signal into the machine learning model and the machine learning may output the predicted delay. In various examples, the machine learning model may predict the delay without utilizing a shape and/or size of the body of the care provider 506 as an input.

In some implementations, the location system may associate the interference signal pattern 510 of the third receiver 504-3, with a positional relationship between the tag 502 and the care provider 506. For instance, the location system may input the signal pattern into a first model, which may output the positional relationship between the tag 502 and the care provider 506. As used herein, the term "positional relationship" can refer to the relative positions of two references. For instance, the positional relationship between the tag 502 and the care provider 506 can be the relative positions of the tag 502 and the care provider 506. In some examples, the location system may predict the delay in the reception of the wireless signal based on the positional relationship. For example, the location system may input the positional relationship into a second model, which may output the predicted delay. In some cases, the second model may also utilize a shape and/or size of the body of the care provider 506 as an input. The shape and/or size of the body of the care provider 506 could be estimated as, for example, a cylinder with a predetermined width (e.g., one foot) and a predetermined height (e.g., six feet). In some cases in which the location system identifies the location of the tag 502 in an x-y (i.e., two-dimensional) coordinate system, the expected volume could be represented by a circular area with a predetermined diameter (e.g., one foot). According to some examples, the expected volume could be based on predetermined measurements of the width and/or height of the care provider 506. The expected volume could therefore be customized to the care provider 506. In some cases, machine learning can be used to identify the shape and/or size of the body of the care provider 506 based on the wireless signal as it is received by any of the receivers 504-1 to 504-3.

In some instances, the location system can predict a direction in which the care provider 506 is facing and predict the delay based on the direction. For instance, the location system may identify that the care provider 506 is moving in a particular direction and may predict that the care provider 506 is also facing in the particular direction. The location system may, for instance, input the predicted angle into a model, which may output the predicted delay. In some cases, the model may also accept, as an input, a location of the receiver (e.g., the first receiver 504-1) that has received the delayed wireless signal. In some cases, the model may also utilize a shape and/or size of the body of the care provider 506 as an input.

In some cases, the location system can predict the direction in which the care provider 506 is facing as well as the relative position between the tag 502 and the care provider 506. In some examples, if the tag 502 is designed to be worn on a lanyard around the neck of the care provider 506, the location system may assume that the tag 502 is positionally located at the front of the care provider's 506 body. Thus, the relative location of the tag 502 with respect to the care provider 506 can be a distance from the care provider 506 in the direction in which the care provider 506 is facing. In some cases, the tag 502 can be predetermined to be 1 inch, 6 inches, or the like from the care provider 506. Based on the direction in which the care provider 506 is facing, the relative position between the tag 502 and the care provider 506, a predicted size and/or shape of the care provider 506, a predicted size and/or shape of the tag 502 itself, and a predicted distance between the tag 502 and the care provider

506, the location system can predict the delay in the reception time of the third receiver 504-3.

In some cases, the location system may identify the probabilities that the care provider 506 is located between the receivers 504-1 to 504-3 based on the positional relationship of the tag 502 and the care provider 506, as well as the direction in which the care provider 506 is facing. For example, the location system may identify an expected volume representing the care provider 506 and identify whether a line projected between an expected position of the tag 502 (e.g., a previous position of the tag 502 or an estimated position of the tag 502 based on the measurements of the receivers 504-1 to 504-3 without adjustment) and a particular receiver intersects the volume. If the location system determines that the line passes through a center portion of the volume, the location system may determine that there is a high likelihood that the care provider 506 is located between the tag 502 and the receiver. If the location system determines that the line passes through a peripheral portion of the volume, the location system may determine that there is a lower likelihood that the care provider 506 is located between the tag 502 and the receiver. If the location system determines that the line does not pass through any portion of the volume, the location system may determine that there is a negligible likelihood that the care provider is located between the tag 502 and the receiver. In some cases, the location system determines the likelihood to be proportional to the amount of the width of the volume that the line intersects. For example, the line passes through the volume by a distance that is equal to the diameter of the volume, the likelihood may be 100%, whereas if the line passes through the volume by a distance that is equal to half of the diameter of the volume, the likelihood may be 50%.

In some cases, the location system may use other strategies for determining the likelihood that the care provider is located between the tag 502 and a given receiver. For example, the location system may identify that a signal strength at the given receiver is lower than an expected value given the timing information. The signal strength may indicate that the wireless signal was attenuated by the body of the care provider 506. Accordingly, the location system may identify that there is a likelihood that the care provider is located between the tag 502 and the receiver based on the signal strength. The location system may predict a delay in the reception time at which a particular receiver receives the wireless signal based on the likelihood.

Based on at least one delay predicted by any of the methods described above, the location system may correct the reception time of the first receiver 504-1 and may identify the location of the tag 502 based on the corrected reception time. For instance, the location system may predict a delay in the reception time at which the particular receiver receives the wireless signal, may adjust the reception time based on the predicted delay, and determine the location of the tag 502 based on the adjusted reception time. In some instances, if the particular receiver measures the time at which the wireless signal is received, the location system may adjust the time to be earlier than the actual time that the signal was received. For example, the location system may assume that the wireless signal is delayed by a particular amount of time (e.g., the predicted delay) due to the body of the care provider 506 and subtract that amount of time from the actual time that the signal was received. In some cases, if the particular receiver measures the angle at which the wireless signal is received, the location system may adjust the angle to be different based on the physics of refraction.

For example, in the example environment 500 depicted in FIG. 5, the location system may determine that there is a high likelihood (e.g., greater than 50% likelihood) that the care provider 506 is located between the tag 502 and the third receiver 504-3 based on the interference signal pattern 510. If the third receiver 504-3 receives a wireless signal 510 emitted by the tag 502 at a particular time $t_1$, the location system may subtract a predetermined delay associated with the body of the care provider 506 from the particular time $t_1$ to generate an adjusted time $t_2$. In some cases, the location system may determine an appropriate delay based on the likelihood (e.g., the delay is proportional to the likelihood), and subtract the appropriate delay from the particular time $t_1$ to generate the adjusted time $t_2$. The location system may estimate the position of the tag 502 as though the third receiver 504-3 received the signal at $t_2$, rather than $t_1$. Furthermore, the location system may determine that there is a relatively low likelihood that the care provider 506 is located between the tag 502 and the first receiver 504-1, as well as a relatively low likelihood that the care provider 506 is located between the tag 506 and the second receiver 504-2. Accordingly, the location system may refrain from adjusting the measurements of the wireless signal by the first and second receivers 504-1 and 504-2 before estimating the position of the tag 502.

Figure 6A:
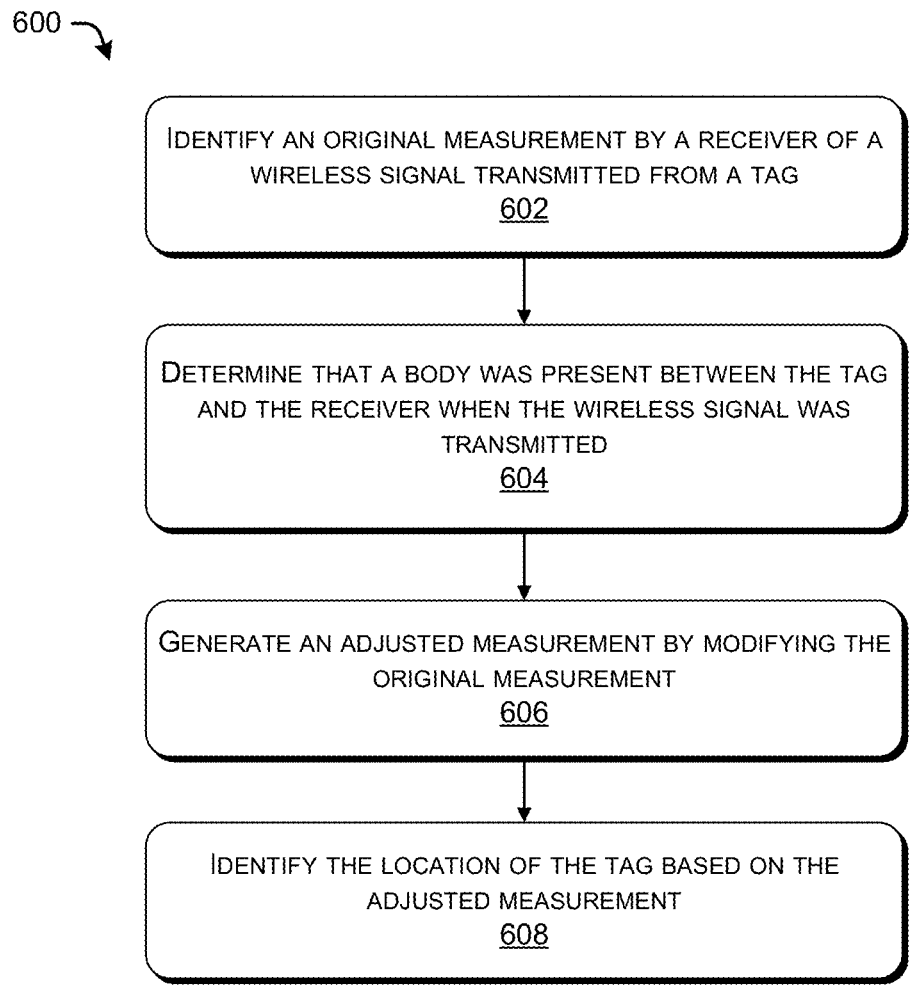
FIGS. 6A and 6B illustrates example processes for taking into account the position of a user in identifying the location of a tag in an environment.

FIG. 6A illustrates an example process 600 for considering the position of a user in identifying the location of a tag in an environment. In some examples, the process 600 can be performed by a location system, such as the location system 808 described below with reference to FIGS. 8 to 10, the location engines 1006 or 1108 described below with reference to FIGS. 10 and 11, or any suitable RTLS.

At 602, the system may identify an original measurement by a receiver of a wireless signal transmitted from a tag. The original measurement may be a reception time of the wireless signal by the receiver. In some cases, the wireless signal may be received over a time interval, and the receiver may generate a a waveform representing a power, intensity, or amplitude of the received wireless signal over time. In some cases, the original measurement may further include a reception time of the wireless signal by the receiver. In some cases, the reception time corresponds to a time associated with a beginning of the time interval, a peak amplitude of the received wireless signal during the time interval, or an end of the time interval.

At 604, the system may determine that a body was present between the tag and the receiver when the wireless signal was transmitted. The body may be a care provider, in some cases. In various examples, the system may assess the shape of the waveform to determine that the shape of the waveform is consistent with an interference signal pattern. For instance, the beginning of the waveform may lack large sharp peaks indicative of a non-interference signal pattern. In some cases, the system may utilize a trained machine learning model to determine that the shape of the waveform indicates that the body was present between the tag and the receiver when the wireless signal was transmitted between the tag and the receiver.

At 606, the system may generate an adjusted measurement by modifying the original measurement. In various implementations, the system may modify the originally identified reception time based on the presence of the body. In some cases, the system may subtract a predetermined delay from the original reception time to generate the adjusted reception time. In various examples, the system may use the machine learning model to identify a delay associated with the specific signal pattern of the received wireless signal and may subtract the identified delay from the original reception time to generate the adjusted reception time.

At 608, the system may identify the location of the tag based on the adjusted measurement. For instance, the system may use the adjusted reception time to estimate the location of the tag in accordance with any of the techniques described herein.

Figure 6B:
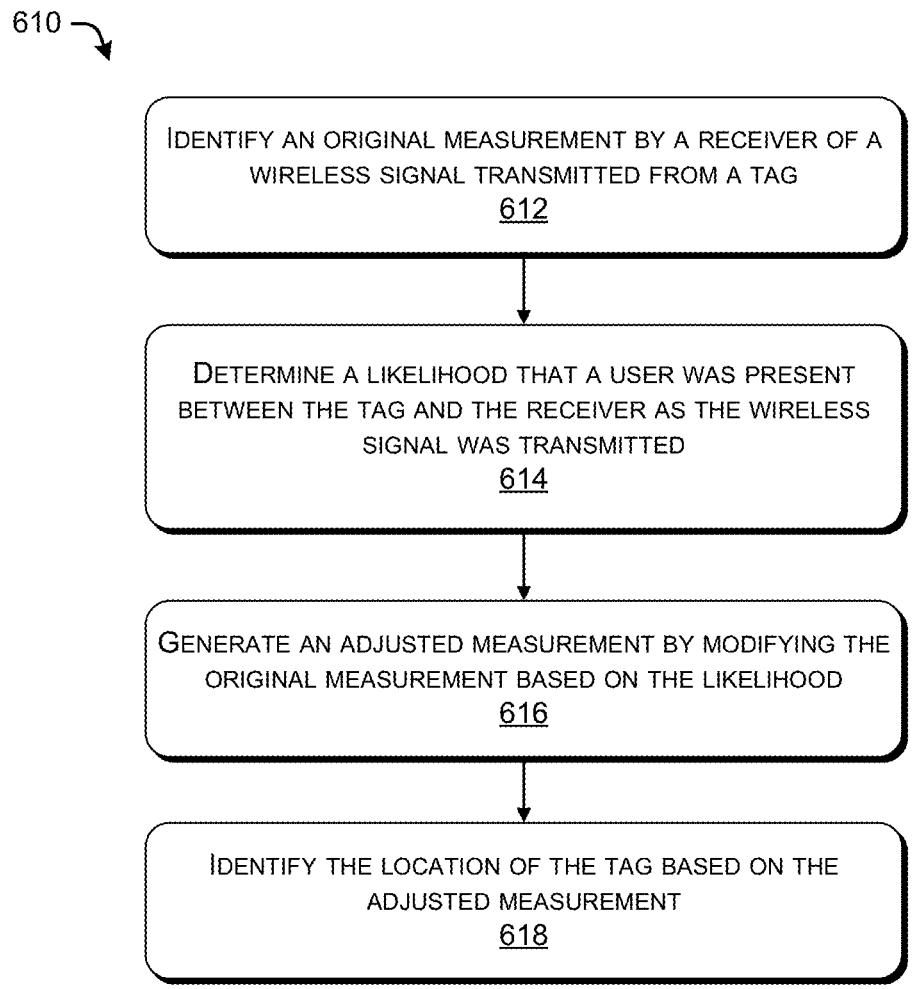

FIG. 6B illustrates an example process 610 for considering the position of a user in identifying the location of a tag in an environment. In some examples, the process 610 can be performed by a location system, such as the location system 808 described below with reference to FIGS. 8 to 10, the location engines 1006 or 1108 described below with reference to FIGS. 10 and 11, or any suitable RTLS.

At 612, the system may identify an original measurement by a receiver of a wireless signal transmitted from a tag. The original measurement may be a timing measurement, in some cases. For instance, the original measurement may be a time-of-flight between the tag and the receiver. In some cases, the original measurement can be a time at which the receiver received the wireless signal from the tag.

At 614, the system may determine a likelihood that a user of the tag was present between the tag and the receiver as the wireless signal was transmitted between the tag and the receiver. In some cases, the system may identify a positional relationship between the tag and the user. For instance, the tag may be predetermined to be attached, worn, or held by the user at a particular side of the user (e.g., front side, right side, left side, back side, or the like). Based on the positional relationship between the tag and the user, as well as the estimated positions of the tag and the receiver, the system can determine the likelihood. In some cases, for the purposes of identifying the estimated position of the tag, the system may presume that the tag is located at a previous location or may estimate the position of the tag based on the original measurement generated by the receiver (without adjustment).

At 616, the system may generate an adjusted measurement by modifying the original measurement identified at 602 based on the likelihood. In some cases, the system may correct for the influence of the user's body on the original measurement. For instance, if the system determines that there is a high likelihood that the user was present between the tag and the receiver, the system may adjust the original measurement accordingly. However, if the system determines that there is a low likelihood that the user was present between the tag and the receiver, the system may refrain from significantly adjusting the original measurement.

At 618, the system may identify the location of the tag based on the adjusted measurement. Accordingly, the influence of the user's body on the measurement used to generate the location can be reduced and/or eliminated.

Figure 7:
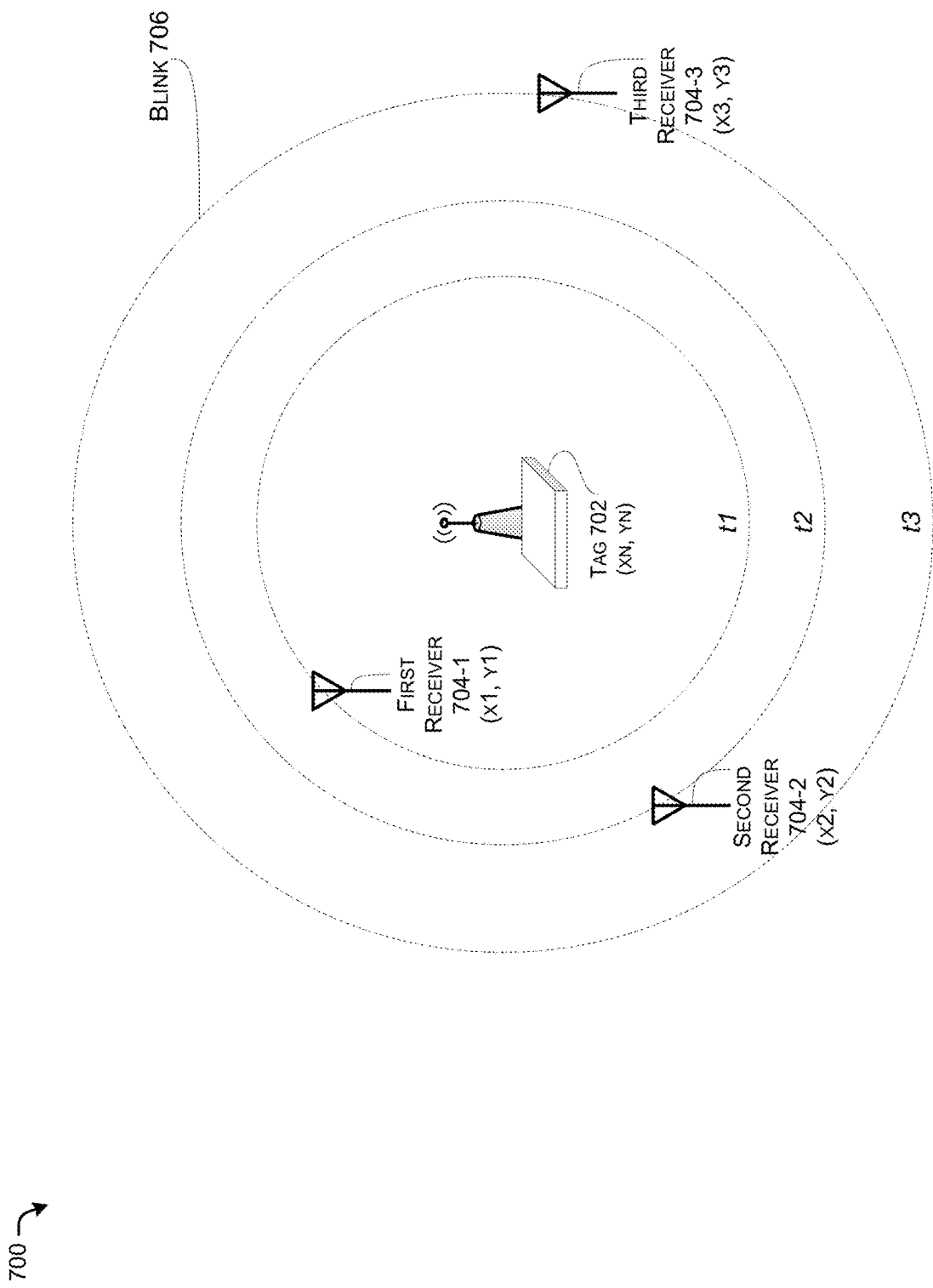
FIG. 7 illustrates an example location system environment.

FIG. 7 illustrates an example location system environment 700. As illustrated, the environment 700 includes a tag 702 and multiple receivers 704-1 to 704-3. In various implementations, the location system can be an RTLS. Various definitions of x, y, and t values used above are not necessarily applicable to the description below. For instance, the $(x_1, y_1)$, $(x_2, y_2)$, and $(x_3, y_3)$ positions described below may be different than the $(x_1, y_1)$, $(x_2, y_2)$, and $(x_3, y_3)$ positions described above with reference to FIGS. 1-6.

In various implementations, the tag 702 is configured to broadcast wireless signals. In some cases, the tag 702 may broadcast the wireless signals periodically. For instance, the tag 702 may be configured to broadcast the wireless signals at a frequency of once every five minutes, once a minute, twice a minute, once every ten seconds, once a second, multiple times per second, or the like. According to some examples in which the tag 702 is carried or affixed by a moving object or person, the tag 702 may broadcast the wireless signals at a frequency of once every 10-1000 milliseconds.

In some cases, the tag 702 may broadcast the wireless signals in response to an event. For instance, the tag 702 may broadcast the wireless signals in response to receiving a request for the wireless signals from another device, or in response to some other type of event. The wireless signals can be electromagnetic signals (e.g., infrared signals, radio signals, etc.), ultrasonic signals, subsonic signals, or the like.

The receivers 704-1 to 704-3 are configured to receive the wireless signals from the tag 702, and to recognize the times at which the wireless signals are received. The receivers 704-1 to 704-3 may be referred to as "anchors" in some cases. In various implementations, the receivers 704-1 to 704-3 are located at known positions. In some implementations, the receivers 704-1 to 704-3 may be mounted at fixed positions on walls, ceilings, or fixtures within a hospital building. The receivers 704-1 to 704-3 may be located at different positions. As illustrated in FIG. 7, a first receiver 704-1 may be located at position $(x_1, y_1)$, a second receiver 704-2 may be located at position $(x_2, y_2)$, and a third receiver 704-3 may be located at a position $(x_3, y_3)$. Although the environment 700 illustrated in FIG. 7 is depicted two dimensions, in some cases, the environment 700 can be defined in three dimensions.

In some cases, the receivers 704-1 to 704-3 may be further configured to communicate with each other over a wired (e.g., ethernet, fiber-optic, etc.) and/or wireless (e.g., Wi-Fi, Bluetooth, etc.) Local Area Network (LAN).

In some implementations, a single wireless signal broadcast by the tag 702 may be referred to as a "blink." As depicted in FIG. 1, an example wireless signal broadcast or blink 706 is transmitted from the tag 702 at time=$t_0$. The blink 706 is received at the first receiver 704-1 at time=$t_1$, at the second receiver 704-1 at time=$t_2$, and at the third receiver 704-3 at time=$t_3$.

The position of the tag 702 may be derived based on the positions of the receivers 704-1 to 704-3 and the times at which the receivers 704-1 to 704-3 receive the blink 706. In various example implementations, the distances between the tag 702 and the receivers 704-1 to 704-3 may be calculated.

In some cases, the blink 706 indicates to. At least one of the receivers 704-1 to 704-3 may be able to derive to from the blink 706. Accordingly, a time-of-flight of the blink 706 between the tag 702 and each one of the receivers 704-1 to 704-3 can be derived according to the following Formula 2:

$$\Delta t = t_n - t_0 \quad \text{Formula 2}$$

wherein $\Delta t$ is the time-of-flight of the blink 706, $t_n$ is the time at which a receiver receives the blink 706 (e.g., $t_1$ for the first receiver 704-1, $t_2$ for the second receiver 704-2, and $t_3$ for the third receiver 704-3), and to is the time at which the tag 702 transmits the blink 706.

Based on the times-of-flight of the blink 706 between the tag 702 and the receivers 704-1 to 704-3, distances between the tag 702 and the receivers 704-1 to 704-3 can be derived based on the following Formula 3:

$$d = \Delta t * v \quad \text{Formula 3}$$

wherein d is the distance between the tag 702 and a particular receiver, $\Delta t$ is the time-of-flight of the blink 706 between the tag 702 and the particular receiver, and v is the velocity of the blink 706. If the blink 706 is an electromagnetic signal, the velocity of the blink 706 can be estimated as the speed of light. If the blink 706 is an ultrasonic or subsonic signal, the velocity of the blink 706 can be estimated as the speed of sound (e.g., through ambient air).

Finally, the position of the tag 702 can be calculated based on the distances between the tag 702 and the receivers 704-1 to 704-3, as well as the known positions of the receivers 704-1 to 704-3. If the position of the tag 702 is defined as $(x_n, y_n)$, the following Formulas 4 can be used to derive the position of the tag 702:

$$d_1^2 = (x_1-x_n)^2 + (y_1-y_n)^2$$

$$d_2^2 = (x_2-x_n)^2 + (y_2-y_n)^2$$

$$d_3^2 = (x_3-x_n)^2 + (y_3-y_n)^2 \quad \text{Formulas 4}$$

wherein $d_1$ is the distance between the first receiver 704-1 and the tag 702, $d_2$ is the distance between the second receiver 704-2 and the tag 702, $d_3$ is the distance between the third receiver 704-3 and the tag 702, $x_1$ is the position of the first receiver 704-1 on the x axis, $y_1$ is the position of the first receiver 704-1 on the y axis, $x_2$ is the position of the second receiver 704-2 on the x axis, $y_2$ is the position of the second receiver 704-2 on the y axis, $x_3$ is the position of the third receiver 704-3 on the x axis, and $y_3$ is the position of the third receiver 704-3 on the y axis.

In some implementations, to may be unknown. In these cases, the position of the tag 702 can be derived by solving for $\underline{x}_n$ and $y_n$ in the following Formulas 5:

$$(v(t_1-t_0))^2 = (x_1-x_n)^2 + (y_1-y_n)^2$$

$$(v(t_2-t_0))^2 = (x_2-x_n)^2 + (y_2-y_n)^2$$

$$(v(t_2-t_0))^2 = (x_3-x_n)^2 + (y_3-y_n)^2 \quad \text{Formulas 5}$$

wherein $t_1$, is the time at which the first receiver 704-1 receives the blink 706, $t_2$ is the time at which the second receiver 704-2 receives the blink 706, $t_3$ is the time at which the third receiver 704-3 receives the blink 706, $t_0$ is the time at which the tag 702 transmits the blink 706, $x_1$ is the position of the first receiver 704-1 on the x axis, $y_1$ is the position of the first receiver 704-1 on the y axis, $x_2$ is the position of the second receiver 704-2 on the x axis, $y_2$ is the position of the second receiver 704-2 on the y axis, $x_3$ is the position of the third receiver 704-3 on the x axis, and $y_3$ is the position of the third receiver 704-3 on the y axis. Using Formulas 5 above, the to term can be eliminated and the $x_n$ and $y_n$ terms can be derived.

In some implementations, one of the receivers 704-1 to 704-3 receives timing information from the other receivers. For instance, the first receiver 704-1 may receive a timing report indicating $t_2$ from the second receiver 704-2 and may receive a timing report indicating $t_3$ from the third receiver 704-3. In some cases, the receiver with the timing information calculates the position of the tag 702. In various examples, the receiver with the timing information forwards the timing information to a location system, which can calculate the location of the tag 702 using the timing information.

According to some implementations, individual receivers among the receivers 704-1 to 704-3 may have differently calibrated clocks. In some cases, each receiver 704-1 to 704-3 may estimate its reception time in its individual time base. To calibrate the different time bases, the first receiver 704-1 may transmit a synchronization signal to the second receiver 704-2 and the third receiver 704-3. The first receiver 704-1 may measure its transmission time ($t_4$) of the synchronization signal. The second receiver 704-2 may measure its reception time of the synchronization signal ($t_5$) and transmit an indication of the reception time to the first receiver 704-1. A first time-of-flight between the first receiver 704-1 and the second receiver 704-2 ($\Delta t_1$) may have been previously identified. The third receiver 704-3 may measure its reception time of the synchronization signal ($t_6$) and transmit an indication of the reception time to the first receiver. A second time-of-flight between the first receiver 704-1 and the third receiver 704-3 ($\Delta t_2$) may have bene previously identified. In various implementations, an offset ($r_1$) between the time base of the first receiver 704-1 and the time base of the second receiver 704-2, as well as an offset ($r_2$) between the time base of the first receiver 704-1 and the time base of the third receiver 704-3, can be calculated according to the following Formulas 6:

$$r_1 = t_5 - (t_4 + \Delta t_1)$$

$$r_2 = t_6 - (t_4 + \Delta t_2) \quad \text{Formulas 6}$$

In various implementations, the offsets $r_1$ and $r_2$ can be applied to any reception times reported by the second receiver 704-2 and the third receiver 704-3 to the first receiver 704-1, in order to ensure that to, $t_1$, $t_2$, $t_3$ are estimated in the same time base.

Figure 8:
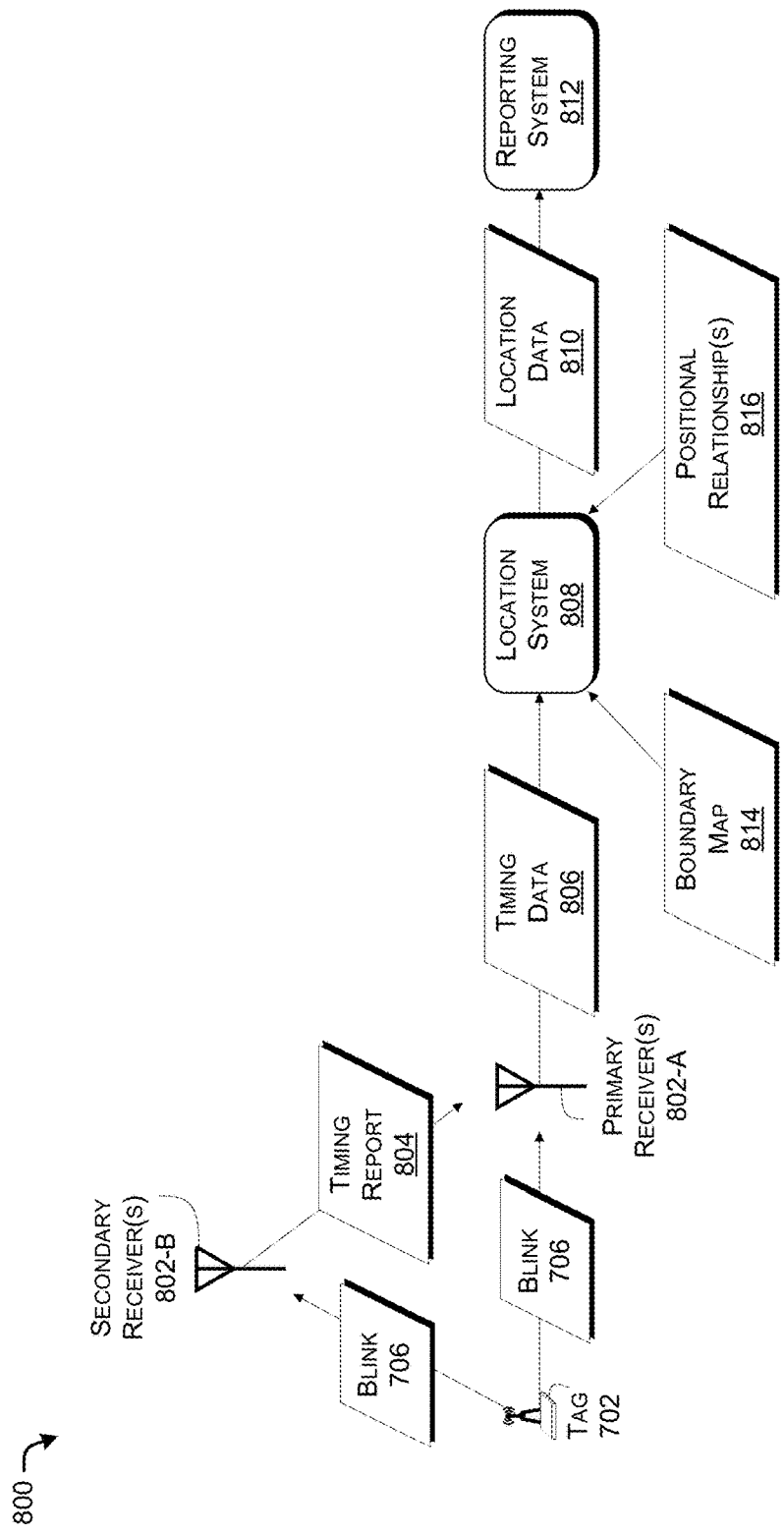
FIG. 8 illustrates an example environment for locating tags in a clinical environment.

FIG. 8 illustrates an example environment 800 for locating tags in a clinical environment. As illustrated, the environment 800 includes the tag 702 transmitting the blink 706, described above with reference to FIG. 7.

As illustrated in FIG. 8, the tag 702 transmits the blink 706 to multiple receivers 802-A and 802-B. In some implementations, the multiple receivers 802-A and 802-B can include the receivers 704-1 to 704-3 described above with reference to FIG. 7. The multiple receivers 802-A and 802-B include primary receiver(s) 802-A and secondary receiver(s) 802-B. The primary receiver(s) 802-A may be connected to the secondary receiver(s) 802-B over a wired and/or wireless Local Area Network (LAN). The secondary receiver(s) 802-B may be configured to identify time(s) when the blink 706 is received by the secondary receiver(s) 802-B and may inform the primary receiver(s) 802-A of the time(s) in a timing report 804. The timing report 804 may be transmitted over the LAN. The primary receiver(s) 802-A may be configured to identify time(s) when the blink 706 is received by the primary receiver(s) 802-A, identify time(s) when the blink 706 is received by the secondary receiver(s) 802-B based on the timing report 804, and may aggregate the times in timing data 806. The primary receiver(s) 802-A may transmit the timing data 806 to a location system 808. In some cases, the timing data 806 may indicate identifiers of the primary receiver(s) 802-A and the secondary receiver(s) 802-B along with the receipt times of the blink 706. In some examples, the timing data 806 may indicate the locations of the primary receiver(s) 802-A and the secondary receiver(s) 802-B along with the receipt times of the blink 706.

In various examples, the primary receiver(s) 802-A and/or the secondary receiver(s) 802-B are configured to transmit the timing data 806 to the location system 808. For example, in some cases, the primary receiver(s) 802-A may transmit a synchronization message (e.g., a wireless broadcast signal) indicating at least one time at which the primary receiver(s) 802-A received the blink 706 from the tag 702. The secondary receiver(s) 802-B may receive the synchronization message from the primary receiver(s) 802-A and may generate the timing data 806 to indicate the time(s) at which the primary receiver(s) 802-A received the blink 706 as well as to indicate at least one time at which the secondary receiver (s) 802-B received the blink 706. The secondary receiver(s) 802-B may transmit the timing data 806 to the location system 808.

The location system 808 may be configured to identify the location of the tag 702 based on the timing data 806. In various implementations, the location system 808 can be a computer system including at least one processor configured to perform operations stored in memory. In some cases, the location system 808 may be able to identify the locations of the primary receiver(s) 802-A and the secondary receiver(s) 802-B by cross-refencing identifiers of the primary receiver(s) 802-A and the secondary receiver(s) 802-B in a database. The identifiers of the primary receiver(s) 802-A and the secondary receiver(s) 802-B may be included in the timing data 806. In some cases, the locations of the primary receiver(s) 802-A and the secondary receiver(s) 802-B may be indicated in the timing data 806 itself.

In various implementations, the location system 808 may be configured to identify the locations of multiple tags including the tag 702. To distinguish the timing data 806 associated with the tag 702 from other timing data associated with other tags, the primary receiver(s) 802-A may generate the timing data 806 indicate the identifier of the tag 702.

Once the location system 808 identifies the location of the tag 702, the location system 808 may indicate the location in location data 810. In some cases, the location data 810 may also indicate the identifier of the tag 702. The location system 808 may transmit the location data 810 to a reporting system 812. The reporting system 812 may output the location of the tag 702 and/or take various other actions based on the location of the tag 702. For instance, if the tag 702 is associated with a care provider and the reporting system 812 determines that the tag 702 is located within the vicinity of a patient in need of immediate care, the reporting system 812 may selectively notify the care provider (e.g., by transmitting a notification to a device associated with the care provider) of the patient's need and request that the care provider attend to the patient.

In various implementations, at least one of the location system 808 and the reporting system 812 may be located outside of an internal network within the clinical environment. At least one firewall may be disposed between the primary receiver(s) 802-A and the location system 808, within the location system 808, between the location system 808 and the reporting system 812, or within the reporting system 812. Accordingly, a security policy within the clinical environment can be enforced.

In various implementations, a boundary map 814 may be utilized by the location system 808 to correct the locations the location system 808 calculates based on the timing data 806. In addition, positional relationship(s) 816 (e.g., between the tag 702 and a user associated with the tag 702) can be utilized by the location system 808 to correct the locations the location system 808 calculates. In some cases, the boundary map 814 and/or the positional relationship(s) 816 can be stored in a local memory of a device implementing the location system 808.

Figure 9:
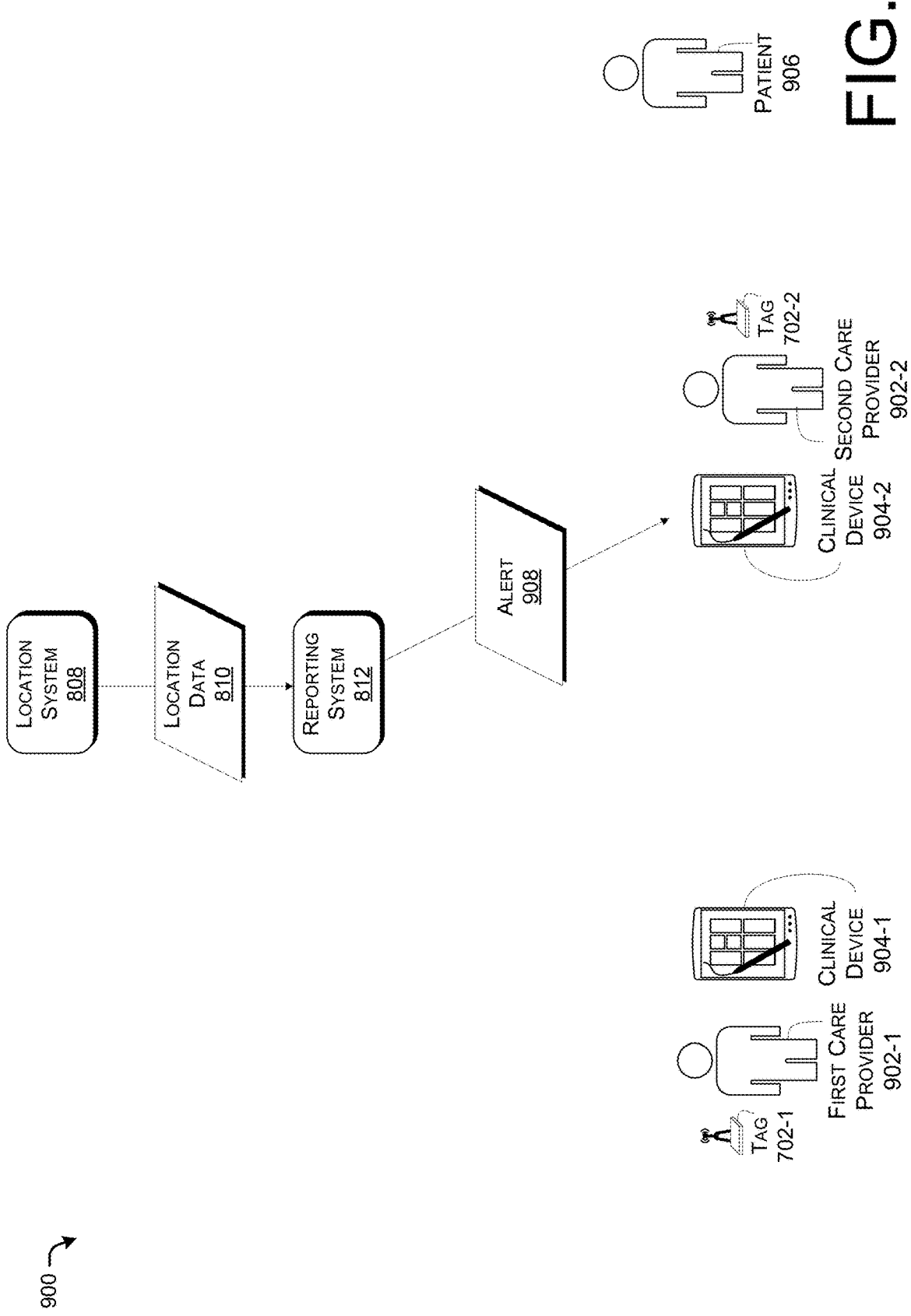
FIG. 9 illustrates an example environment of a location system being utilized in a clinical environment.

FIG. 9 illustrates an example environment 900 of a location system 808 being utilized in a clinical environment. As noted above, the location system 808 may provide the reporting system 812 with the location data 810. The location data 810 may indicate the locations of various tags (e.g., tag 702) throughout the clinical environment. In the example illustrated in FIG. 9, the location data 810 may indicate the locations of first and second tags 702-1 and 702-2 in the clinical environment.

First tag 702-1 may be worn by, held by, or attached to clinical provider 902-1. Clinical provider 902-1 may be associated with a clinical device 904-1. The clinical device 904-1 may be a mobile device, in some cases. In various implementations, the clinical device 904-1 could output alerts, instructions, or the like, to assist the clinical provider 902-1 with treating and monitoring patients within the clinical environment.

Similarly, second tag 702-2 may be worn by, held by, or attached to clinical provider 902-2. Clinical provider 902-2 may be associated with a clinical device 904-2. The clinical device 904-2 may be a mobile device, in some cases. In various implementations, the clinical device 904-2 could output alerts, instructions, or the like, to assist the clinical provider 902-2 with treating and monitoring patients within the clinical environment.

In various implementations, the reporting system 812 may identify that a patient 906 is in need of assistance from a clinical provider, such as either one of clinical providers 902-1 or 902-2. For example, the reporting system 812 may identify that the patient 906 is in need of non-emergency care (e.g., changing of a wound dressing, drug administration, or the like) or emergency care (e.g., defibrillation, tracheostomy, or the like). The reporting system 812 may also be aware of the location of the patient 906.

In some instances, the reporting system 812 may compare the location data 810 to the location of the patient to identify which one of the tags 702-1 or 702-2 is closest to the patient 906. Based on this comparison, the reporting system 812 may identify that the tag 702-2 is closest to the patient 906. In some cases, the reporting system 812 may identify that the tag A02-2 associated with the second care provider 902-2 is within a predetermined distance of the patient 906. According to various examples, the reporting system 812 may determine that the tag 702-2 is within the same room as the patient 906, is within a predetermined distance (e.g., 10 feet, 20 feet, etc.) of the patient, is the closest available care provider to the patient 906, or the like. In some cases, the reporting system 812 may determine that the tag 702-2 is closer to the patient 906 than the tag 702-1.

The reporting system 812 may identify that the tag 702-2 is associated with the second care provider 902-2 and/or the clinical device 904-2 utilized by the second care provider 902-2. The reporting system 812 can selectively transmit an alert 908 to the clinical device 904-2. In response to receiving the alert, the clinical device 904-2 may output an instruction to provide assistance to the patient 906.

Figure 10:
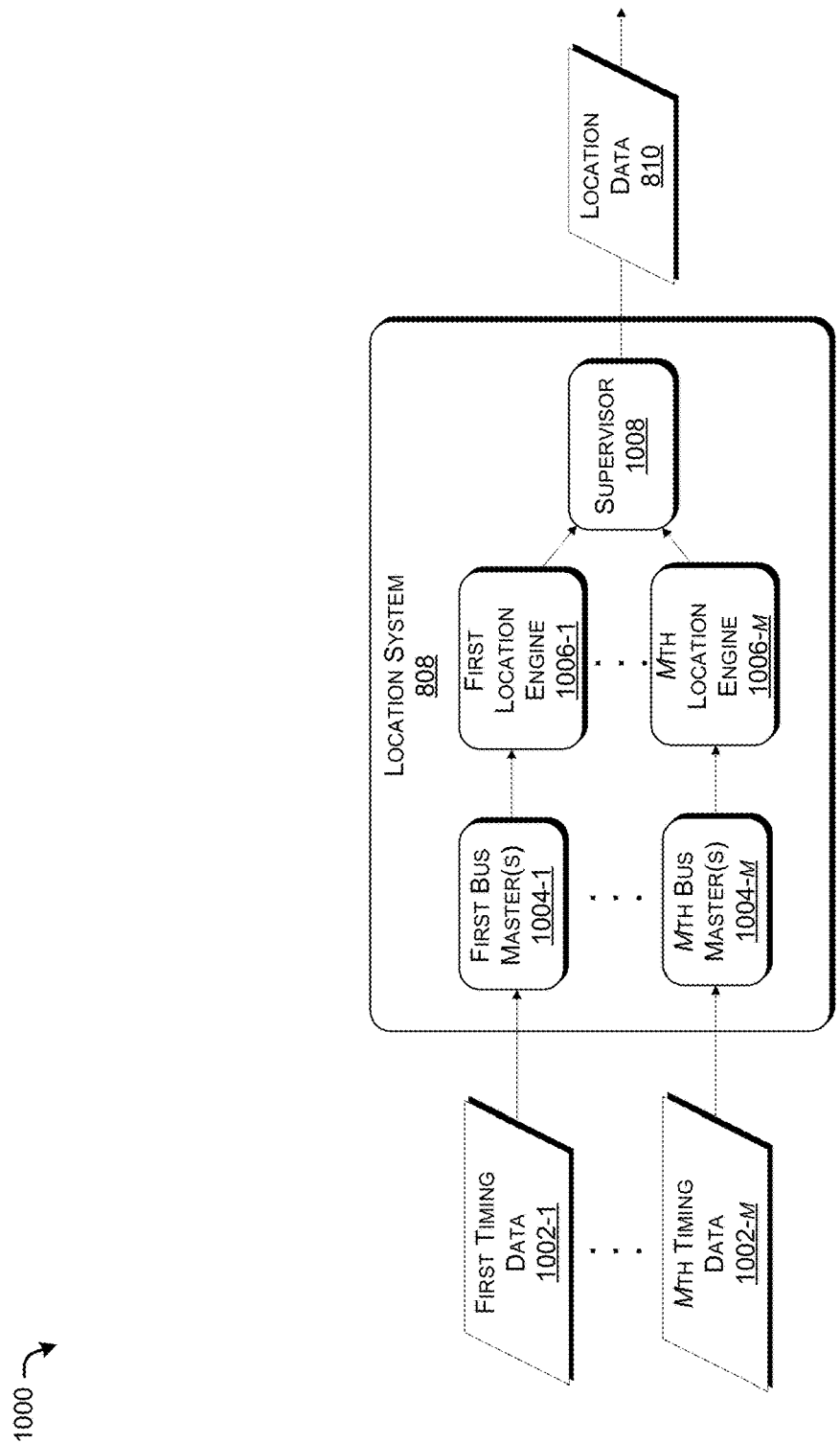
FIG. 10 illustrates an example environment for determining the locations of multiple tags in a clinical environment.

FIG. 10 illustrates an example environment 1000 for determining the locations of multiple tags in a clinical environment. As illustrated, the environment 1000 includes the location system 808 and the location data 810 described above with reference to FIG. 8.

First through mth timing data 1002-1 to 1002-*m* may be received at first to mth bus masters 1004-1 to 1004-*m* in the location system 808. The timing data 1002-1 to 1002-*m* may represent timing data from multiple receivers receiving signals from multiple tags in the clinical environment. For instance, first timing data 1002-1 may represent timing data from multiple primary receivers based on blinks from multiple tags. In some cases, the timing data 1002-1 to 1002-*m* can be represented in data streams transferred from the primary receivers to the first to mth bus masters 1004-1 to 1004-*m*.

The bus masters 1004-1 to 1004-*m* may each include hardware and/or software including a serial connection to which multiple receivers (e.g., multiple primary receivers) are connected. In various implementations, the bus masters 1004-1 to 1004-*m* may be configured to orchestrate communications between the multiple receivers and other network nodes within the location system 806. In some cases, the bus masters 1004-1 to 1004-*m* are connected to other network nodes within the location system 806 via a Local Area Network (LAN).

In some cases, the bus masters 1004-1 to 1004-*m* may generate individual data packets associated with single blink events (e.g., the same blink from the same tag) and transmit the individual data packets to the location engines 1006-1 to 1006-*m*. When the bus masters 1004-1 to 1004-*m* receive timing data 1002-1 to 1002-*m* from multiple primary receivers based on the same blink event, the bus masters 1004-1 to 1004-*m* may be able to aggregate the subset of the timing data 1002-1 to 1002-*m* from the same blink event into individual data packets.

The locating engines 1006-1 to 1006-*p* may be configured to calculate the locations of the tags based on the data received from the bus masters 1004-1 to 1004-*m*. In some cases, p<m, such that there is a greater number of bus masters 1004-1 to 1004-*m* than locating engines 1006-1 to 1006-*p*. For instance, multiple bus masters 1004-1 to 1004-*m* may be connected to a single one of the locating engines 1006-1 to 1006-*p*.

A single supervisor (also referred to as an "aggregator") 708 may receive indications of the calculated locations from the location engines 1006-1 to 1006-*p*. The single supervisor 1008 may aggregate the locations into location data 810. The location data 810 may be in the form of a data stream indicating individual tags and their calculated locations.

According to various implementations, one or more of the bus masters 1004-1 to 1004-*m*, locating engines 1006-1 to 1006-*p*, and aggregator 708 may be network nodes.

Figure 11:
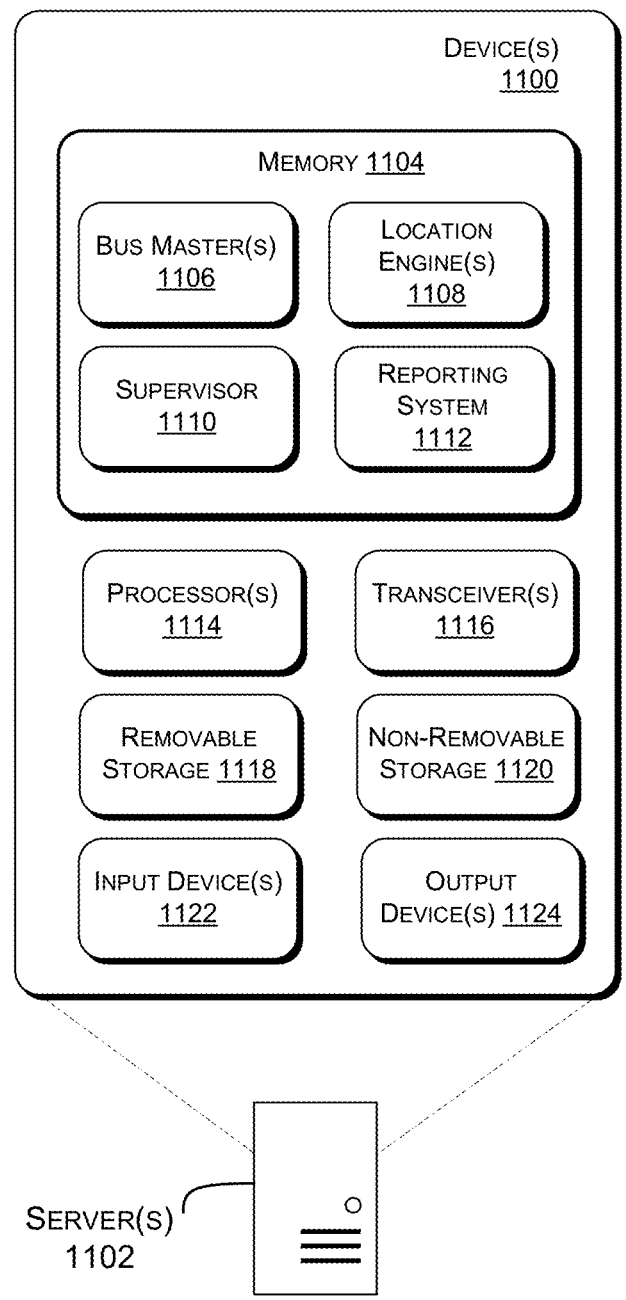
FIG. 11 illustrates at least one example device configured to enable and/or perform the some or all of the functionality discussed herein.

FIG. 11 illustrates at least one example device 1100 configured to enable and/or perform the some or all of the functionality discussed herein. Further, the device(s) 1100 can be implemented as one or more server computers 1102, a network element on a dedicated hardware, as a software instance running on a dedicated hardware, or as a virtualized function instantiated on an appropriate platform, such as a cloud infrastructure, and the like. It is to be understood in the context of this disclosure that the device(s) 1100 can be implemented as a single device or as a plurality of devices with components and data distributed among them.

As illustrated, the device(s) 1100 comprise a memory 1104. In various embodiments, the memory 504 is volatile (including a component such as Random Access Memory (RAM)), non-volatile (including a component such as Read Only Memory (ROM), flash memory, etc.) or some combination of the two.

The memory 1104 may include various components, such as at least one bus master 1106, at least one location engine 1108, a supervisor 1110, a reporting system 1112, and the like. Any of the bus master(s) 1106, the location engine(s) 1108, the supervisor 1110, and the reporting system 1112 can comprise methods, threads, processes, applications, or any other sort of executable instructions. The bus master(s) 1106, the location engine(s) 1108, the supervisor 1110, and the reporting system 1112 and various other elements stored in the memory 1104 can also include files and databases.

The memory 1104 may include various instructions (e.g., instructions in the bus master(s) 1106, location engine(s) 1108, supervisor 1110, and/or reporting system 1112), which can be executed by at least one processor 1114 to perform operations. In some embodiments, the processor(s) 1114 includes a Central Processing Unit (CPU), a Graphics Processing Unit (GPU), or both CPU and GPU, or other processing unit or component known in the art.

The device(s) 1100 can also include additional data storage devices (removable and/or non-removable) such as, for example, magnetic disks, optical disks, or tape. Such additional storage is illustrated in FIG. 11 by removable storage 1118 and non-removable storage 1120. Tangible computer-readable media can include volatile and nonvolatile, removable and non-removable media implemented in any method or technology for storage of information, such as computer readable instructions, data structures, program modules, or other data. The memory 1104, removable storage 1118, and non-removable storage 1120 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 1100. Any such tangible computer-readable media can be part of the device(s) 1100.

The device(s) 1100 also can include input device(s) 1122, such as a keypad, a cursor control, a touch-sensitive display, voice input device, etc., and output device(s) 1124 such as a display, speakers, printers, etc. These devices are well known in the art and need not be discussed at length here. In particular implementations, a user can provide input to the device(s) 500 via a user interface associated with the input device(s) 1122 and/or the output device(s) 1124.

As illustrated in FIG. 11, the device(s) 1100 can also include one or more wired or wireless transceiver(s) 1116. For example, the transceiver(s) 1116 can include a Network Interface Card (NIC), a network adapter, a Local Area Network (LAN) adapter, or a physical, virtual, or logical address to connect to the various base stations or networks contemplated herein, for example, or the various user devices and servers. To increase throughput when exchanging wireless data, the transceiver(s) 1116 can utilize Multiple-Input/Multiple-Output (MIMO) technology. The transceiver(s) 1116 can include any sort of wireless transceivers capable of engaging in wireless, Radio Frequency (RF) communication. The transceiver(s) 1116 can also include other wireless modems, such as a modem for engaging in Wi-Fi, WiMAX, Bluetooth, or infrared communication.

In some implementations, the transceiver(s) 1116 can be used to communicate between various functions, components, modules, or the like, that are comprised in the device(s) 1100. For instance, the transceivers 1116 may facilitate communications between the bus master(s) 1106, the location engine(s) 1108, the supervisor 1110, and/or the reporting system 1112.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Although the subject matter has been described in language specific to structural features and/or methodological acts, it is to be understood that the subject matter defined in the appended claims is not necessarily limited to the specific features or acts described.

The invention claimed is:

1. A location system, comprising:
   at least one transceiver;
   at least one processor; and
   memory storing instructions that, when executed by the at least one processor, cause the at least one processor to perform operations comprising:
   identifying a first position of a tag in a clinical environment based on a first wireless signal received by first receivers from the tag, the first wireless signal being transmitted by the tag at a first transmission time;
   determining an estimated second position of the tag in the clinical environment based on a second wireless signal received by second receivers from the tag, the second wireless signal being transmitted by the tag at a second transmission time;
   determining, using a boundary map of the clinical environment, that a boundary is located between the first position and the estimated second position;
   defining a path range substantially surrounding the first position of the tag based on an estimated movement of the tag, from the first position to the estimated second position, during a time interval between the first transmission time and the second transmission time;
   determining, using the boundary map of the clinical environment, that the boundary lacks a door within the path range;
   estimating a corrected second position of the tag in the clinical environment based on the estimated second position of the tag and the boundary map; and
   transmitting, to a reporting system using the at least one transceiver, a message indicating that the tag is located at the corrected second position at the second transmission time.

2. The location system of claim 1, wherein the operations further comprise:
   receiving, by the at least one transceiver from a first primary receiver among the first receivers, first timing data indicating first reception times at which the first receivers received the first wireless signal from the tag; and
   receiving, by the at least one transceiver from a second primary receiver among the second receivers, second timing data indicating second reception times at which the second receivers received the second wireless signal from the tag,
   wherein determining the first position of the tag is based on the first reception times and third positions at which the first receivers receive the first wireless signal in the clinical environment, and
   wherein determining the estimated second position of the tag is based on the second reception times at fourth positions at which the second receivers receive the second wireless signal in the clinical environment.

3. The location system of claim 1, wherein the boundary map is stored in the memory and indicates locations of boundaries including the boundary and locations of doors including the door in the clinical environment, the boundaries including at least one of a wall, a fence, or a window.

4. The location system of claim 1, wherein defining the path range comprises:
   determining a walking speed of a user associated with the tag based on previous movements of the user in the clinical environment;
   generating a walking distance based on a product of the walking speed and the time interval;
   generating a path radius based on a sum of the walking distance and a predetermined error of the location system; and
   defining the path range as a circle surrounding the first position, a radius of the circle being the path radius.

5. The location system of claim 1, wherein estimating the corrected second position comprises:
   identifying a line segment between the first position and the estimated second position;
   determining an intersection point at which the line segment intersects the boundary; and
   defining the corrected second position at the intersection point.

6. The location system of claim 1, wherein the corrected second position is located between the first position and the boundary.

7. The location system of claim 1, wherein the tag is associated with a user, the location system further comprising:
   a reporting system configured to determine that a patient is located within a predetermined distance of the corrected second position and to transmit an alert to an electronic device associated with the user upon determining that the patient is located within the predetermined distance of the corrected second position.

8. A method, comprising:
   determining a first position of a tag in a clinical environment based on first receivers receiving a first wireless signal from the tag, the first wireless signal being transmitted by the tag at a first transmission time;
   determining an estimated second position of the tag in the clinical environment based on second receiving a second wireless signal from the tag, the second wireless signal being transmitted by the tag at a second transmission time;
   determining, using a boundary map of the clinical environment, that a boundary is located between the first position and the estimated second position;
   defining a path range substantially surrounding the first position of the tag based on an estimated movement of the tag, from the first position to the estimated second position, during a time interval between the first transmission time and the second transmission time;
   determining, using the boundary map of the clinical environment, that the boundary comprises a door within the path range; and
   transmitting, to a reporting system using the at least one transceiver, a message indicating that the tag is located at the estimated second position at the second transmission time.

9. The method of claim 8, further comprising:
   receiving, by the at least one transceiver from a first primary receiver among the first receivers, first timing data indicating first reception times at which the first receivers received the first wireless signal from the tag; and
   receiving, by the at least one transceiver from a second primary receiver among the second receivers, second timing data indicating second reception times at which the second receivers received the second wireless signal from the tag, wherein determining the first position of the tag is based on the first reception times and third positions of the first receivers in the clinical environment, and wherein determining the estimated second position of the tag is based on the second reception times at fourth positions of the second receivers in the clinical environment.

10. The method of claim 8, wherein the boundary map indicates locations of boundaries including the boundary and locations of doors including the door in the clinical environment, the boundaries including at least one of a wall, a fence, or a window.

11. The method of claim 8, wherein defining the path range comprises:
   determining a walking speed of a user associated with the tag based on previous movements of the user in the clinical environment;
   generating a walking distance based on a product of the walking speed by the time interval;
   generating a path radius based on a sum of the walking distance and a predetermined error of the location system; and
   defining the path range as a circle surrounding the first position of the tag, a radius of the circle being the path radius.

12. The method of claim 8, wherein the tag is associated with a user, the method further comprising:
   determining that the estimated second position is within a predetermined distance of a patient; and
   transmitting an alert to an electronic device associated with the user upon determining that the patient is located within the predetermined distance of the corrected second position.

13. A location system, comprising:
   a receiver;
   at least one processor; and
   memory storing instructions that, when executed by the at least one processor, cause the processor to perform operations comprising:
      identifying an original time at which the receiver receives a wireless signal transmitted from a tag in a clinical environment;
      determining that a user associated with the tag was located between the tag and the receiver as the wireless signal was transmitted from the tag to the receiver;
      generating an adjusted time by modifying the original time; and
      identifying the location of the tag based on the adjusted time.

14. The location system of claim 13, wherein the receiver is a primary receiver, and identifying the original time comprises:
   receiving, from secondary receivers, a timing report indicating multiple other times at which the secondary receivers in the clinical environment received the wireless signal;
   generating, by the primary receiver, timing data indicating the original time and the multiple other times; and
   identifying the location of the tag based on the adjusted time and the multiple other times.

15. The location system of claim 13, wherein determining that the user was located between the tag and the receiver comprises:
   identifying a waveform of an amplitude of the wireless signal received by the receiver over time;
   determining, based on the shape of the waveform, that the user was located between the tag and the receiver.

16. The location system of claim 13, wherein determining that the user was located between the tag and the receiver comprises:
   identifying a predetermined position of the receiver;
   determining an estimated position of the tag based on the original time;
   determining a relative position of the tag with respect to the user; and
   determining, based on the predetermined position of the receiver, the estimated position of the tag, and the relative position of the tag, that the user associated with the tag was located between the tag and the receiver.

17. The location system of claim 16, wherein determining the relative position of the tag with respect to the user comprises:
   identifying that the tag is positioned on a front side of the user;
   determining a direction in which the user is moving; and
   determining that the tag is positioned a predetermined distance from the user in the direction in which the user is moving.

18. The location system of claim 13, wherein generating the adjusted time comprises:
   identifying an estimated delay of the wireless signal associated with traveling through the user; and
   generating the adjusted time by subtracting the estimated delay from the original time.

19. The location system of claim 13, wherein the operations further comprise:
   transmitting, to a reporting system, a message indicating that the tag is at the location.

20. The location system of claim 19, further comprising:
   the reporting system configured to determine that a patient is within a predetermined distance of the location and to transmit an alert to an electronic device associated with the user upon determining that the patient is located within the predetermined distance of the location.

* * * * *